US007547793B2

(12) United States Patent
Hallahan et al.

(10) Patent No.: US 7,547,793 B2
(45) Date of Patent: Jun. 16, 2009

(54) METHOD FOR MAKING INSECT REPELLENT COMPOSITION

(75) Inventors: David L. Hallahan, Wilmington, DE (US); Leo Ernest Manzer, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 203 days.

(21) Appl. No.: 11/474,595

(22) Filed: Jun. 26, 2006

(65) Prior Publication Data
US 2006/0240079 A1    Oct. 26, 2006

Related U.S. Application Data

(63) Continuation of application No. 10/664,544, filed on Sep. 18, 2003, now abandoned.

(51) Int. Cl.
C07D 311/02    (2006.01)
(52) U.S. Cl. .................................................. 549/283
(58) Field of Classification Search ................. 549/273, 549/283
See application file for complete search history.

(56) References Cited

U.S. PATENT DOCUMENTS

| 4,416,881 | A | 11/1983 | McGovern et al. |
| 4,469,613 | A | 9/1984 | Munteanu et al. |
| 4,496,467 | A | 1/1985 | Munteanu et al. |
| 4,548,764 | A | 10/1985 | Munteanu et al. |
| 4,663,346 | A | 5/1987 | Coulston et al. |
| 4,869,896 | A | 9/1989 | Coulston et al. |
| 5,753,686 | A | 5/1998 | Marin et al. |
| 6,462,015 | B1 | 10/2002 | Weiss et al. |
| 6,524,605 | B1 | 2/2003 | Coats et al. |
| 7,067,677 | B2 * | 6/2006 | Manzer ................ 549/283 |
| 7,067,678 | B2 * | 6/2006 | Scialdone ............. 549/283 |
| 7,232,844 | B2 * | 6/2007 | Hallahan .............. 514/456 |
| 2003/0073748 | A1 | 4/2003 | Henderson et al. |
| 2003/0191047 | A1 | 10/2003 | Hallan |
| 2004/0024054 | A1 | 2/2004 | Haenke |

FOREIGN PATENT DOCUMENTS

| EP | 0 167 265 B1 |   | 1/1986 |
| EP | 0 450 087 A1 |   | 4/1991 |
| EP | 0 450 087 A1 |   | 10/1991 |
| WO | WO 03/079786 | * | 3/2003 |
| WO | WO 03/084946 | * | 4/2003 |
| WO | WO 03/086069 A2 |   | 10/2003 |

OTHER PUBLICATIONS

U.S. Appl. No. 10/405,444, filed Apr. 5, 2003, Leo Ernest Manzer.
C. E. Schreck et. al., Activity of Repellents Applied to Skin for Protection Against Amblyomma Americanum and Ixodes Scapularis Ticks (Acari: Ixodidae), Journal of the American Mosquito Association, 1995, vol. 11:136-140.

R. K. M. Hay et. al., Botany Volatile Oil Crops, Their Biology and Production, 1993, pp. 5-22.
L. J. Clark et. al., Analysis of Monoterpenoids in Glandular Trichomes of the Calmint Nepeta Racemosa. The Plant Journal, 1997, vol. 11:1387-1393.
G. Briassoulis et. al., Toxic Encephalopathy Associated With Use of Deet Insect Repellents: A Case Analysis of its Toxicity in Children, Human & Experimental Toxicology, 2001, vol. 20:8-14.
Chris Peterson et. al., Insect Repellents—Past, Present and Future, Pesticide Outlook, Aug. 2001.
C. Peterson, Abstracts of Paper American Chemical Society, 2001, vol. 222:1-2.
T. Eisner, Science, 1965, vol. 148:966-968.
T. Eisner, Science, 1964, vol. 146:1318-1320.
T. Hollon, For Tomorrow's Infantry:SS-220, A Gunsight Friendly Insect Repellent, The Scientist, 2003, pp. 25-26.
H. Inouye, Iridoids, Methods in Plant Biochemistry, 1991, vol. 7:99-143.
New Scientist, The Sweet Smell of Death, 1996, pp. 28-31.
Pesticide Outlook, Pesticides Based on Plant Essential Oils, 1999, pp. 68-72.
Lena B. Brattsten, Cytochrome P-450 Involement in the Interactions Between Plant Terpenes and Insect Herbivores, 1983, pp. 173-195.
Abstract of Braveman, Y. Mosquito Repellent Attracts Culicoides Imicola, (Diptera: Ceratopogonidae), Journal of Medical Entomology, 1999, vol. 36:113-115.
Ramanathan Natarajan et. al., Chirality Index, Molecular Overlay and Biological Activity of Diastereoisomeric Mosquito Repellents, Pest Management Science, 2005, vol. 61:1193-1201.
Arthur O. Tucker et. al., Catnip and the Catnip Response, Economic Botany, 1988, vol. 42:214-231.
Jefson et. al., Chemical Defense of a Rove Bettle, Journal of Chemical Ecology, 1983, vol. 9:150-180.
G.W.K. Cavill et. al., Defensive and Other Secretions of the Australian Cocktail Ant, Iridomyrmex Nitidiceps, Tetrahedron, 1982, vol. 38:1931-1938.
G.W.K. Cavill et. al., Insect Venoms, Attractants, and Repellents—VIII, Isohihydronepetalactone, J. Insect Physiol., 1967, vol. 13:131-135.
Abstract of Krell, Frank-Thorsten et. al., Dung Beetles Attracted by a Commerical Insect Repellent, Entomologists Monthly Magazine, 2003, vol. 139:1667-1669.
Uyehara et. al., Cyclisation of A,B,X,U-Unsaturated Dioic Acids Esters Via Tandem Conjugate Additions by Using Lithium-Benzyltrimethylsilylamide (LSA) as a Nitrogen Nucleophile and its (+) Isodihydronepetalactone, J. Chem. Soc., Chem. Commum., 1989, pp. 113-114.

(Continued)

Primary Examiner—D. Margaret Seaman
Assistant Examiner—Nizal S Chandrakumar

(57) ABSTRACT

Dihydronepetalactone, a minor natural constituent of the essential oil of catmints (*Nepeta* spp.) such as *Nepeta cataria*, has been identified as an effective insect repellent compound. Synthesis of dihydronepetalactone may be achieved by hydrogenation of nepetalactone, the major constituent of catmint essential oils. This compound, which also has fragrance properties, may be used commercially for its insect repellent properties, and methods for making an composition thereof are disclosed.

15 Claims, 11 Drawing Sheets

OTHER PUBLICATIONS

Lee et. al., Stereoselective Favorskii Rearrangement of Carvone Chlopohydrin:Expedient Synthesis of (+) Dihydronepetalactone and (+) Iridomyrmecin, J. Chem. Soc., Chem. Commun., 1994, pp. 479-481.

Tanimori et. al., Total Synthesis of (+) Dihydronepetalactone, Agric. Biol. Chem., 1991, vol. 55:1181-11832.

C.J. Peterson et. al., Catnip Essential Oil as a Barrier to Subterranean Termites (Isoptera: Rhinotermitidae) in the Laboratory, Household and Structural Insects, J. Econ. Entomol., 1998, vol. 4:1275-1282.

International Search Report dated Jul. 11, 2003.

Abelman et. al., Alicyclic Claisen Rearrangement, A General Carbocycle Synthesis Based on Four-Atom-Ring Contractions of Lactones, J. Am. Chem. Soc., 1982, vol. 104:4030-4032.

Fleming et. al., Stereospecific Allylisilane Reactions: A Total Synthesis of Dihydronepetalactone, Tetrahedron Letters, 1984, vol. 25:5103-5104.

Fleming et. al., Sterocontrol in Organic Synthesis Using Silicon-Containing Compounds, A Synthesis of (+) Dihydronepetalactone Using the SE2 Reaction of an Allysilane, J. Chem. Soc., Perkin Trans, 1998, vol. 1:2645-2649.

Nagata et. al., Concurrent Resolution and Oxidation of an Allylic Acetate and its Utilization in the Diastereocontrolled Synthesis of Some Cyclopentanoid Monterpenes, Tetrahedron Letters, 1999, vol. 40:6617-6620.

Nangia et. al., Intramolecular Horner-Wadsworth-Emmons Reaction in Base Sensitive Substrates: Enantiospecific Synthesis of Iridold Monoterpene Lactones, Tetrahedron Letters, 1994, vol. 35:3755-3758.

Uyehara et. al., New Type of Cyclization of a B,X Unsaturated Dioic Acid Esters Through Tandem Conjugate Additions by Using Lithium N-Benzyl-N (Trimethylsilyl) Amide as a Nitrogen Nucleophile, J. Org. Chem., 1992, vol. 57:3139-3145.

Wolinsky et. al., Syntheses of the Dihydronepetalactones, J. Org. Chem., 1972, vol. 37:3376-3378.

Wolinsky et. al., The Synthesis of (+) Matatabiether and Related Methylcyclopentane Monoterpenes, Tetrahedron, 1969, vol. 25:3767-3774.

Barasa et. al., Repellent Activities of Stereoisomers of P-Menthane 3,8 Diols Against Anopheles Gambiae (Diptera: Culicidae), J. Med. Entomol., 2002, vol. 39:736-741.

Barnard et. al., Global Collaboration for Development of Pesticides for Public Healthy, (GCDPP) Wolrd Health Organization, pp. 1-49, 2000.

Bergmann et. al., Study of Synthetic Compounds as Repellents Against the Mosquitoes Culex Pipiens Molestus and Aedes Aegypti, Israel Journal of Entomollgy, 1976, vol. XI, pp. 15-61.

Dawson et. al., The Aphid Sex Pheromone, Pure & Appl. Chem., 1989, vol. 61:555-558.

R. Lilley et. al., The Aphid Sex Pheromone: A Novel Host Location Cue for the Parasitoid Praon Volucre, Brighton Crop Protection Conference—Pests and Disease, 1994, pp. 1157-1162.

W.A. Skinner et. al., The Design of Insect Repellents, Drug Design, 1980, vol. X,:278-305.

Regnier et. al., Studies on the Composition of the Essential Oils of Three Nepeta Species, Phytochemistry, 1967, vol. 6:1281-1289.

Depooter et. al., The Essential Oils Five Nepeta Species. A Preliminary Evaluation of Their Use in Chemotaxonomy by Cluster Analysis, Flavour and Fragrance Journal, 1988, vol. 3:155-159.

Handjieva et. al., Constituents of Essential Oils From Nepeta Cataria L., N. Grandiflora M.B. and N. Nuda L., J. Essential Oil Res., 1996, vol. 8:639-643.

Fradin et. al., Comparative Efficacy of Insect Repellents Against Mosquito Bites, New England Journal of Medicine, 2002, vol. 347:13-18.

H.S. Fogler, Elementary Chemical Reaction Engineering, Prentice-Hall (Book Not Included), 1996.

Augustine, Heterogeneous Catalysis for the Synthetic Chemist, 1996, Marcel Decker, 1996, (Book Not Included.

* cited by examiner

Figure 1    Structures of (7S)-nepetalactones
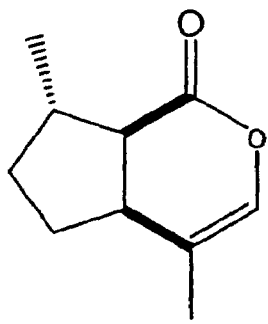
(4aS,7S,7aR) nepetalactone
(cis,trans-nepetalactone)
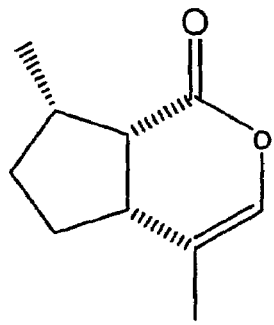
(4aR,7S,7aS) nepetalactone
(cis,cis-nepetalactone)
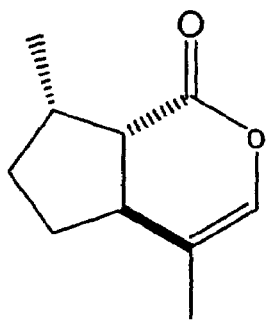
(4aS,7S,7aS) nepetalactone
(trans,cis-nepetalactone)
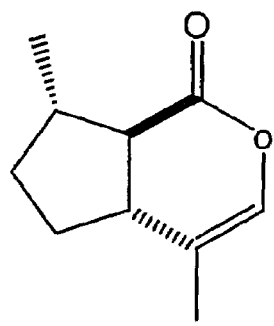
(4aR,7S,7aR) nepetalactone
(trans,trans-nepetalactone)

Figure 2    Total ion chromatograms from GC-MS analysis of fractionally distilled catmint oil before (A) and after (B) hydrogenation.
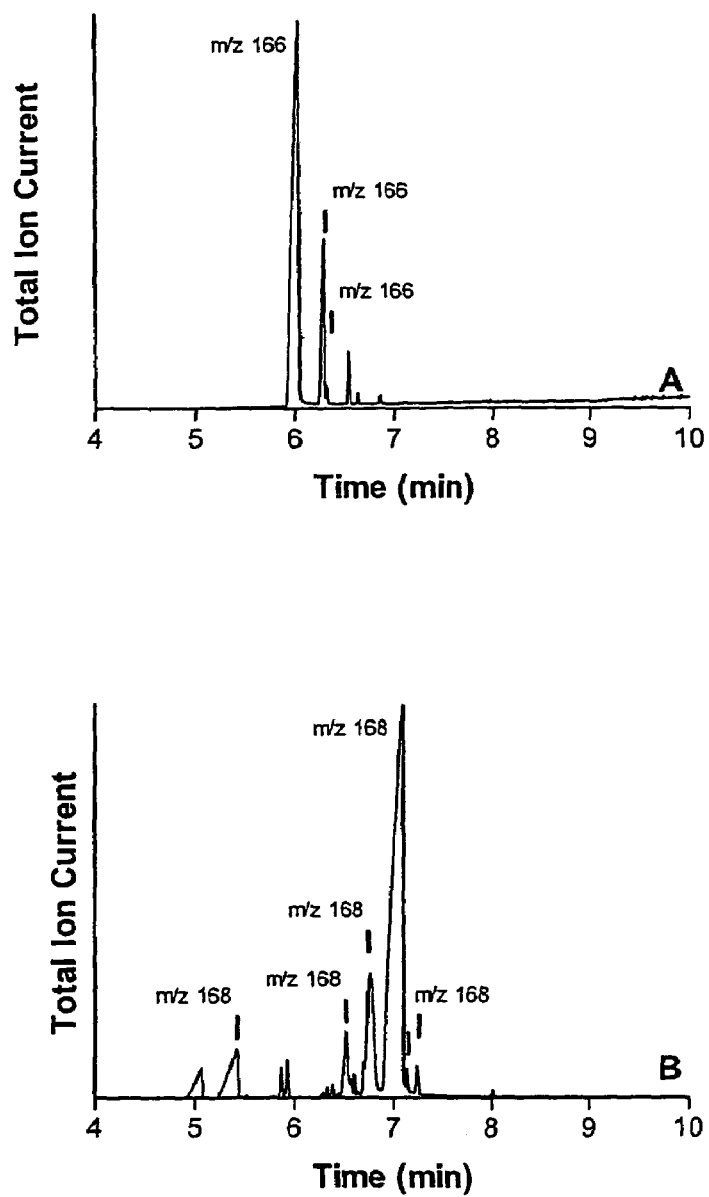

Figure 3  Mass spectra of nepetalactone (A) and dihydronepetalactone (B) peaks from GC-MS analysis.
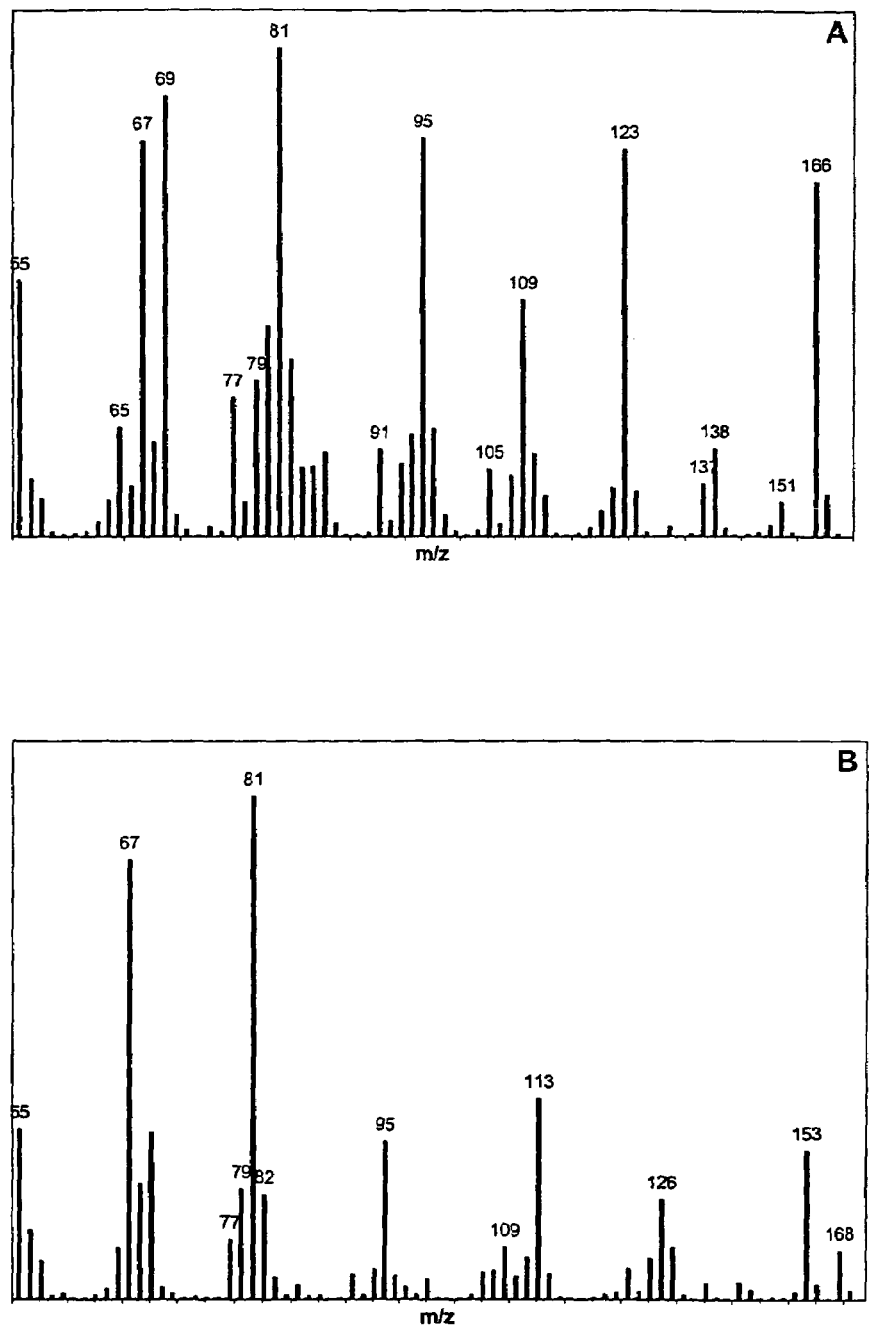

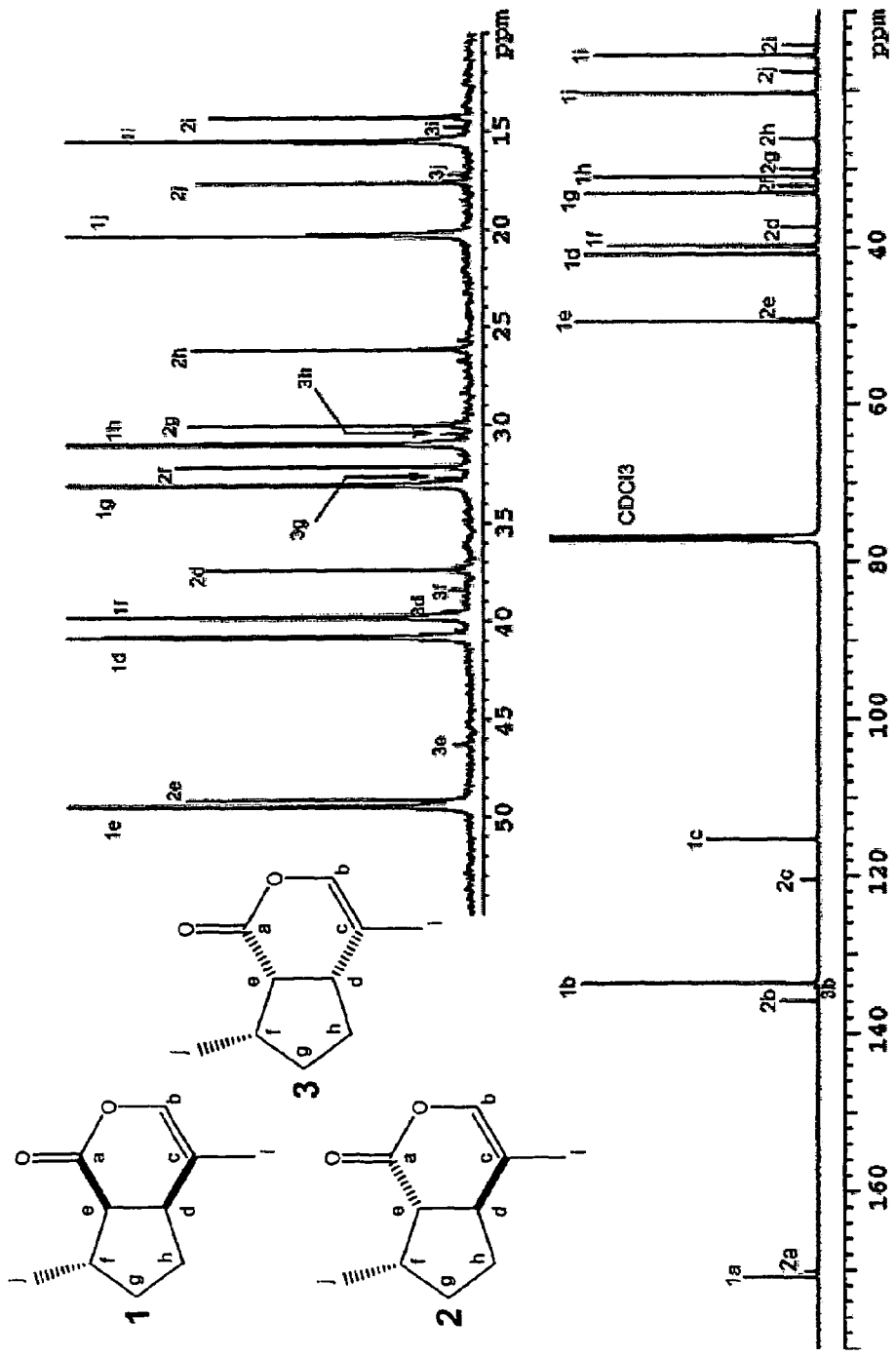
Figure 4  $^{13}$C NMR analysis of nepetalactones in fractionally-distilled catmint oil.

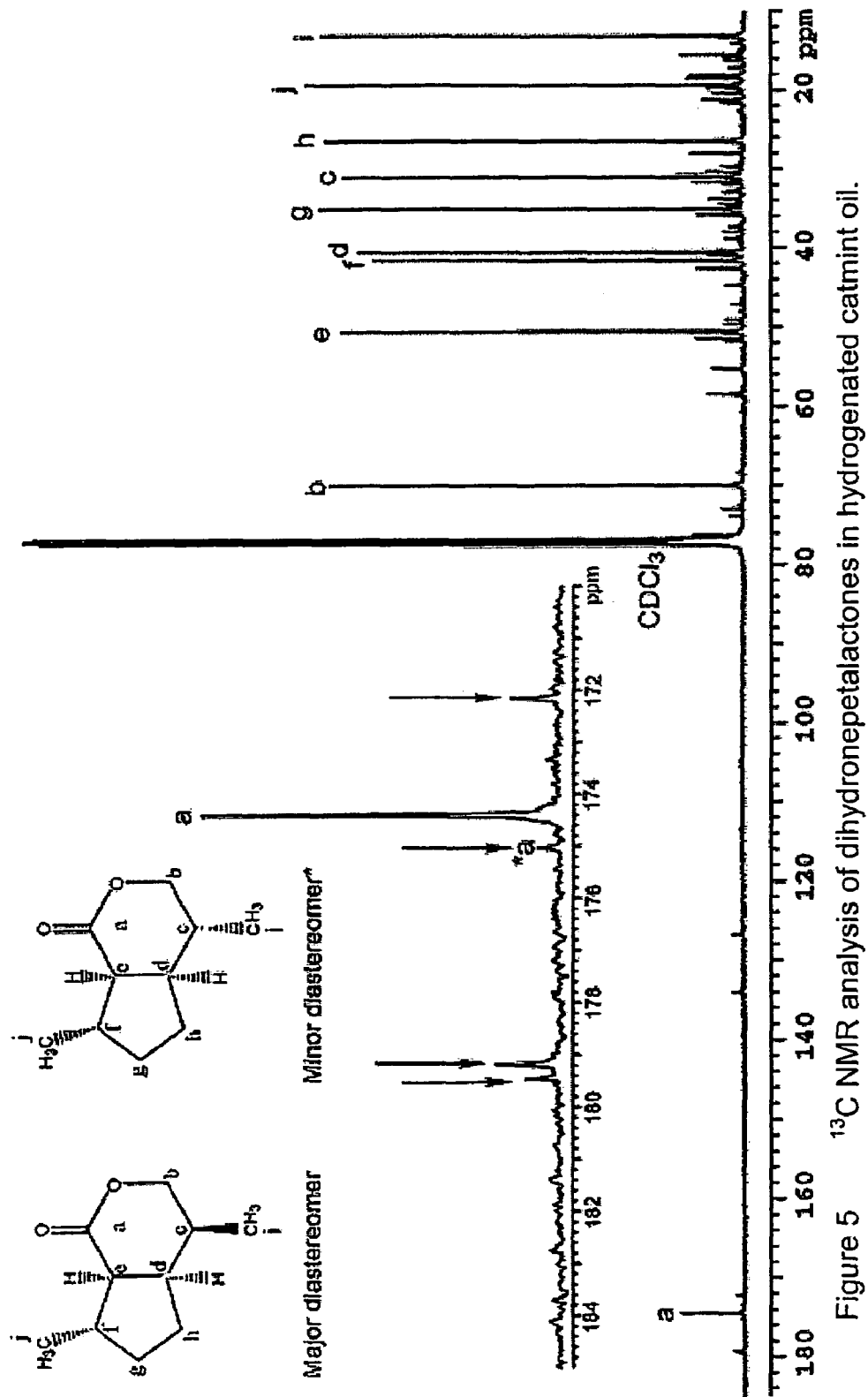
Figure 5 $^{13}$C NMR analysis of dihydronepetalactones in hydrogenated catmint oil.

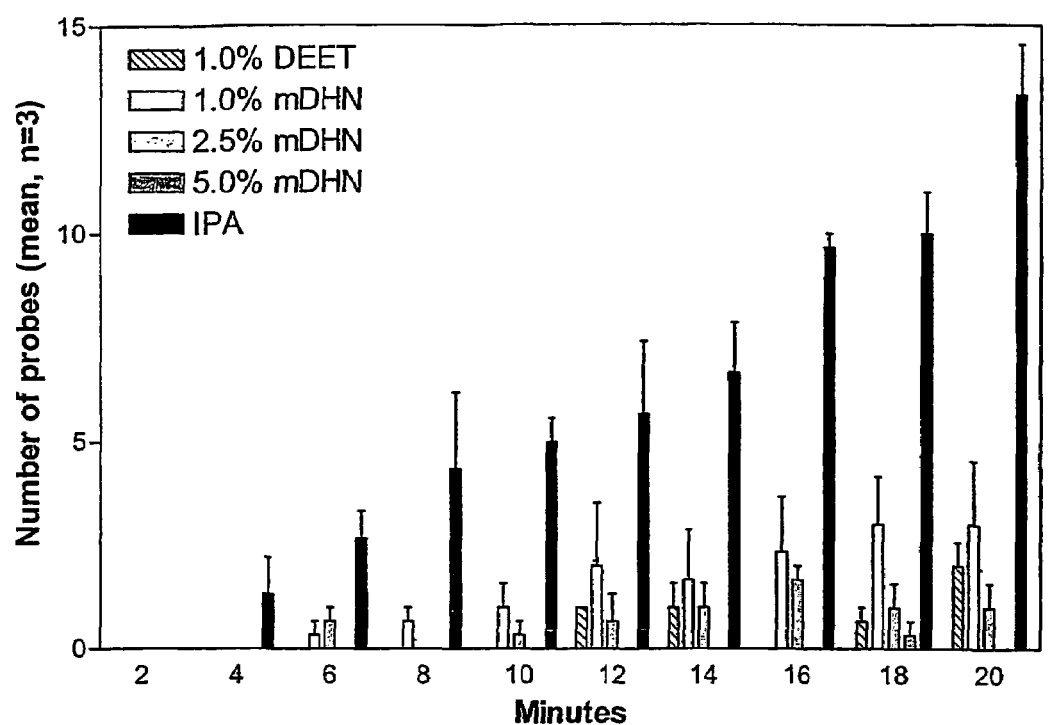
Figure 6 Distribution of probing density over time (*Aedes aegypti* mosquitoes; dihydronepetalactones derived from hydrogenation of a mixture of nepetalactone stereoisomers).

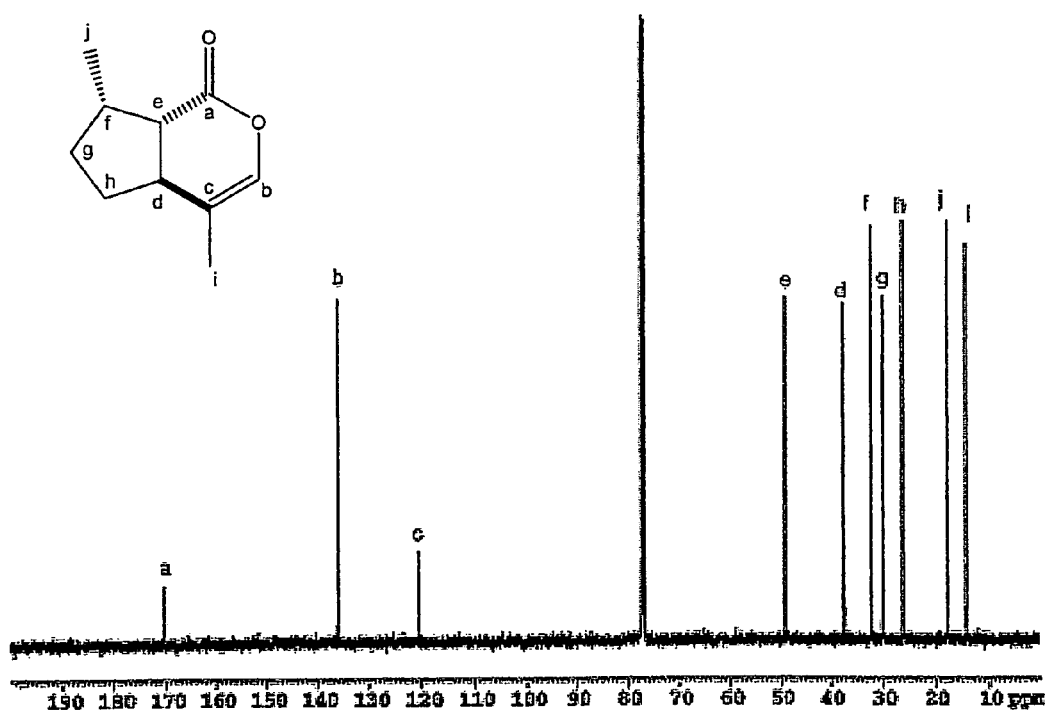
Figure 7    $^{13}$C NMR analysis of *trans,cis*-nepetalactone.

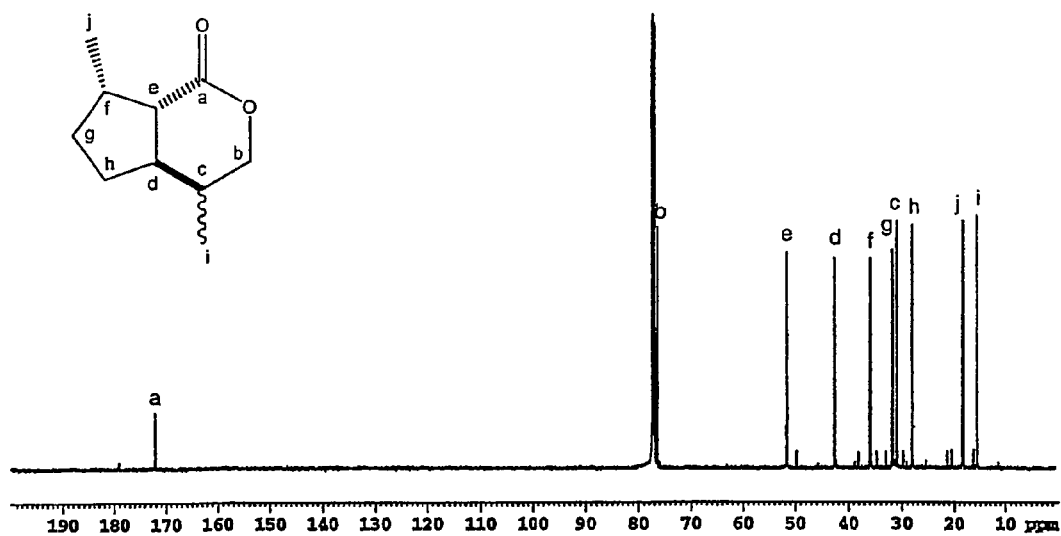
Figure 8   $^{13}$C NMR analysis of dihydronepetalactones derived from hydrogenation of *trans,cis*-nepetalactone.

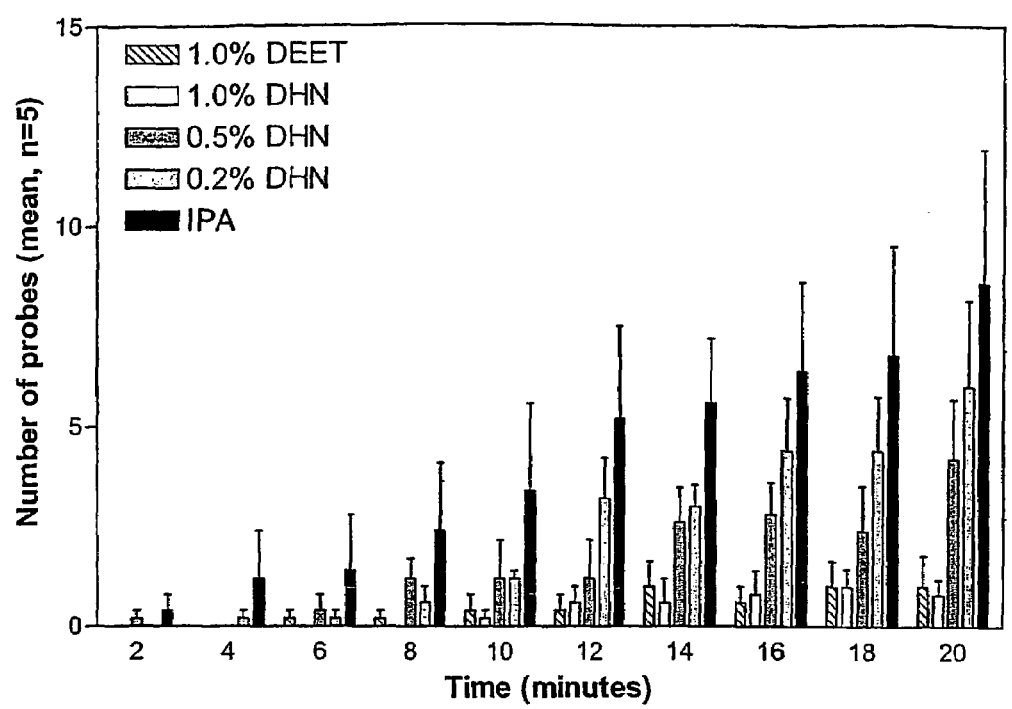
Figure 9  Distribution of probing density over time (*Aedes aegypti* mosquitoes; dihydronepetalactones derived from hydrogenation of *trans,cis*-nepetalactone).

Fig. 10    Distribution of landing density with time, during tests of various repellents against stable flies (*Stomoxys calcitrans*).

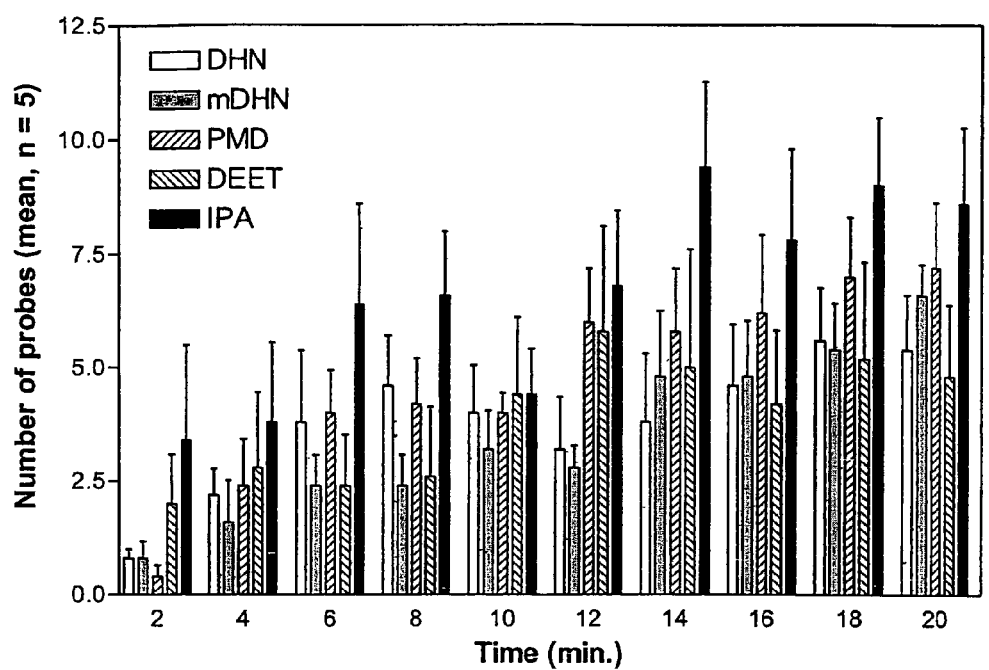
Fig. 11 Distribution of probing density with time, during tests of various repellents against anopheles mosquitoes (*A. albimanus*).

METHOD FOR MAKING INSECT REPELLENT COMPOSITION

This application is a continuation of U.S. application Ser. No. 10/664,544, filed Sep. 18, 2003, which is a continuation-in-part of U.S. application Ser. No. 10/392,455, filed Mar. 19, 2003, each of which is incorporated in its entirety as a part hereof for all purposes.

FIELD OF THE INVENTION

The present invention relates to the field of insect repellency, and to a method for making a composition containing one or more dihydronepetalactone stereoisomers for use as a repellent material.

BACKGROUND OF THE INVENTION

Repellent substances generally cause insects to be driven away from, or to reject, otherwise insect-acceptable food sources or habitats. At least 85% of insect repellent sales in the United States are for insect repellents containing N,N-diethyl-m-toluamide (DEET) as their primary active ingredient. Further, *Consumer Reports* tests indicated that products with the highest concentration of DEET lasted the longest against mosquitoes. Although an effective repellent, DEET possesses an unpleasant odor and imparts a greasy feeling to the skin. Other disadvantages associated with DEET include: 1) it is a synthetic chemical, that is, it is not derived from natural sources; 2) it exhibits a somewhat limited spectrum of activity—it is not, for example, as effective as might be desired against black-legged or deer ticks (Schreck, C. E., Fish, D. & McGovern, T. P. (1995) Journal of the American Mosquito Control Association 11 (1), 136-140); 3) DEET dissolves or mars many plastics and painted surfaces; and 4) DEET may plasticize some inert ingredients typically used in topical formulations which leads to lower user acceptability.

As a result of the above limitations, DEET-free products with repellent activity are finding favor with consumers. In particular, demand for compositions containing natural products is increasing. New candidate repellents should possess a desirable balance of properties, and will preferably reach or exceed the positive properties of DEET, and/or not suffer from its negative properties (Hollon, T. (2003) The Scientist Jun. 16, 2003, 25-26).

Many plant species produce essential oils (aromatic oils) which are used as natural sources of insect repellent and fragrant chemicals [Hay, R. K. M., Svoboda, K. P., *Botany*, in 'Volatile Oil Crops: their biology, chemistry and production'. Hay, R. K. M., Waterman, P. G. (eds.). Longman Group UK Limited (1993)]. Citronella oil, known for its general repellence towards insects, is obtained from the graminaceous plants *Cymbopogon winterianus* and *C. nardus*. Examples of plants used as sources of fragrant chemicals include *Melissa officinalis* (Melissa), *Perilla frutescens* (Perilla), *Pososternon cablin* (Patchouli) and various *Lavandula* spp. (Lavender). All of these examples of plants yielding oils of value are members of the Labiatae (Lamiaceae) family. Plants of the genus *Nepeta* (catmints) are also members of this family, and produce an essential oil that is a minor item of commerce. This oil is very rich in a class of monoterpenoid compounds known as iridoids [Inouye, H. *Iridoids. Methods in Plant Biochemistry* 7:99-143 (1991)], more specifically the methylcyclopentanoid nepetalactones [Clark, L. J. et al. *The Plant Journal*, 11:1387-1393 (1997)] and derivatives.

Iridoid monoterpenoids have long been known to be effective repellents to a variety of insect species (Eisner, T. (1964) *Science* 146:1318-1320; Eisner, T. (1965) *Science* 148:966-968; Peterson, C. and Coats, J. (2001) *Pesticide Outlook* 12:154-158; Peterson, C. et al. (2001) *Abstracts of Papers American Chemical Society* 222 (1-2): AGRO73). Studies of the repellency of catnip oil (predominantly nepetalactone) showed that it was repellent towards a number of insect species on short-term exposure, but not to a number of other species (Eisner, T. (1964) *Science* 146:1318-1320).

U.S. Pat. No. 4,663,346 discloses insect repellants with compositions containing bicyclic iridoid lactones (e.g., iridomyrmecin). Further, U.S. Pat. No. 4,869,896 discloses use of these bicyclic iridoid lactone compositions in potentiated insect repellent mixtures with DEET. U.S. Pat. No. 6,524,605 discloses insect repellents comprising nepetalactones derived from the catmint plant *N. cataria*, and the differential efficacy of nepetalactone stereoisomers as insect repellents.

Compositions containing dihydronepetalactones (DHN), a class of iridoid monoterpenoids derived from nepetalactones (shown in FIG. 1), are known to provide insecticidal effects. For example, a study of the composition of the secretion from anal glands of the ant *Iridomyrmex nitidus* showed that isodihydronepetalactone was present in appreciable amounts, together with isoiridomyrmecin (Cavill, G. W. K., and D. V. Clark. (1967) *J. Insect Physiol.* 13:131-135). Isoiridomyrmecin was known at the time to possess good 'knockdown' insecticidal activity.

Cavill et al. (1982) (*Tetrahedron* 38:1931-1938), discloses the presence of dihydronepetalactones in the insect repellent secretion of an ant but the compound iridodial is said to be the principal repellent constituent.

Jefson, M., et al. (1983) (*J. Chemical Ecology* 9:159-180) disclose dihydronepetalactone to exhibit effective repellency in the vapor phase to ants over a period of 25 seconds. Longer times were not investigated. After 25 seconds of exposure to vapors from the pure dihydronepetalactone, approximately 50-60% of *Monomorium destructor* ants ceased to feed. No indication was given in regard to the duration of the repellent effect.

SUMMARY OF THE INVENTION

One embodiment of this invention is an insect repellent composition of matter that is or includes a dihydronepetalactone, or a mixture of dihydronepetalactone stereoisomers, represented by the general formula:

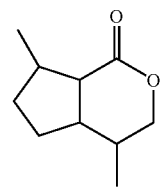

Another embodiment of this invention is a composition of matter that repels insects when applied to a human, animal or inanimate host that includes a dihydronepetalactone, or a mixture of dihydronepetalactone stereoisomers, represented by the general formula set forth above.

A further embodiment of this invention is a composition of matter that repels one or more insects selected from the group consisting of bees, black flies, chiggers, fleas, green head flies, mosquitoes, stable flies, ticks, wasps, wood-boring insects, houseflies, cockroaches, lice, roaches, wood lice, flour and bean beetles, dust mites, moths, silverfish, and weevils, that includes a dihydronepetalactone, or a mixture of dihydronepetalactone stereoisomers, represented by the general formula set forth above.

Yet another embodiment of this invention is a process for fabricating an insect repellent composition or an insect repellent article of manufacture by providing as the composition or article, or incorporating into the composition or article, a dihydronepetalactone, or a mixture of dihydronepetalactone stereoisomers, represented by the general formula set forth above.

Yet another embodiment of this invention is a method of repelling insects from a human, animal or inanimate host by exposing the insects to a dihydronepetalactone, or a mixture of dihydronepetalactone stereoisomers, represented by the general formula set forth above. The insects repelled may be, for example, one or more of mosquitoes, stable flies and ticks.

Yet another embodiment of this invention is the use of a dihydronepetalactone, or a mixture of dihydronepetalactone stereoisomers, represented by the general formula above to repel insects from a human, animal or inanimate host. The insects repelled may be, for example, one or more of mosquitoes, stable flies and ticks.

Yet another embodiment of this invention is a method of preparing a composition comprising a dihydronepetalactone, or a mixture of dihydronepetalactone diastereomers, represented by the general formula above, by (a) providing an herbaceous material that comprises the genus *Nepeta* (catmint), (b) extracting from the herbaceous materials an oil that comprises nepetalactone, (c) contacting the oil with hydrogen in the presence of a hydrogenation catalyst, but in the absence of a diluent, to provide a 9-S dihydronepetalactone, and (d) recovering the 9-S dihydronepetalactone so produced and admixing it with a carrier and/or a cosmetic adjuvant.

Yet another embodiment of this invention is a method of preparing a composition comprising a dihydronepetalactone, or a mixture of dihydronepetalactone diastereomers, represented by the general formula above, by (a) providing an herbaceous material that comprises the genus *Nepeta* (catmint), (b) extracting from the herbaceous materials an oil that comprises nepetalactone, (c) contacting the oil with hydrogen in the presence of a hydrogenation catalyst, and in the presence of an alcohol diluent, to provide a 9-S dihydronepetalactone, and (d) recovering the 9-S dihydronepetalactone so produced as a mixture with the alcohol diluent.

Applicants have found that dihydronepetalactones perform well as a new class of effective insect repellent compounds without the disadvantageous properties characteristic of prior-art compositions. When used as an insect repellent, DHN prevents damage to plants and animals, including humans, or to articles of manufacture, by making insect food sources or living conditions unattractive or offensive.

BRIEF DESCRIPTION OF THE DRAWINGS

FIG. 1 shows the chemical structures of the naturally-occurring iridoid (methylcyclopentanoid) nepetalactones.

FIG. 2 shows the total ion chromatograms from combined gas chromatography/mass spectrometry (GC-MS) analysis of a distilled nepetalactone-enriched fraction from commercially-available catmint oil (A), together with that of the material produced from this fraction by hydrogenation (B).

FIG. 3 shows the mass spectra of the major constituents of the nepetalactone-enriched fraction (A) and the hydrogenated material (B) identified by GC-MS analysis in FIG. 2.

FIG. 4 shows the $^{13}$C NMR analysis performed on a distilled nepetalactone-enriched fraction of commercially-available catmint oil.

FIG. 5 shows the $^{13}$C NMR spectrum obtained from analysis of the dihydronepetalactones produced by hydrogenation of a distilled nepetalactone-enriched fraction of commercially-available catmint oil FIG. 6 shows the distribution of probing density with time, during tests of various repellents against female *Aedes aegypti* mosquitoes in an in vitro repellency test.

FIG. 7 shows the $^{13}$C NMR analysis of trans,cis-nepetalactone.

FIG. 8 shows the $^{13}$C NMR analysis of dihydronepetalactones derived from hydrogenation of trans,cis-nepetalactone.

FIG. 9 shows the distribution of probing density with time, during tests of dihydronepetalactones derived from hydrogenation of trans,cis-nepetalactone against female *Aedes aegypti* mosquitoes in an in vitro repellency test.

FIG. 10 shows the distribution of landing density with time, during tests of various repellents against stable flies (*Stomoxys calcitrans*) in an in vitro repellency test.

FIG. 11 shows the distribution of probing density with time, during tests of various repellents against female *anopheles* mosquitoes (*Anopheles albimanus*) in an in vitro repellency test.

DESCRIPTION OF A PREFERRED EMBODIMENT OF THE INVENTION

A nepetalactone is a compound having the general structure:

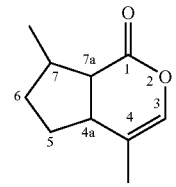

Four chiral centers are present within the methylcyclopentanoid backbone of nepetalactone at carbons 4, 4a, 7 and 7a as shown above; (7S)-nepetalactones are produced by several plants and insects.

Dihydronepetalactones are known as minor constituents of the essential oils of several labiate plants of the genus *Nepeta* (Regnier, F. E., et al. (1967) *Phytochemistry* 6:1281-1289; DePooter, H. L., et al. (1988) *Flavour and Fragrance Journal* 3:155-159; Handjieva, N. V. and S. S. Popov (1996) *J. Essential Oil Res.* 8:639-643). Dihydronepetalactones are defined by Formula 1:

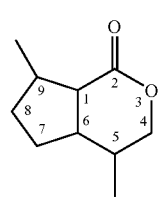

Formula 1 wherein 1, 5, 6 and 9 indicate the four chiral centers of the molecule and the structure shown is intended to encompass all stereoisomers of dihydronepetalactone. The structures of dihydronepetalactone stereoisomers that may be derived from (7S)-nepetalactones are shown below.

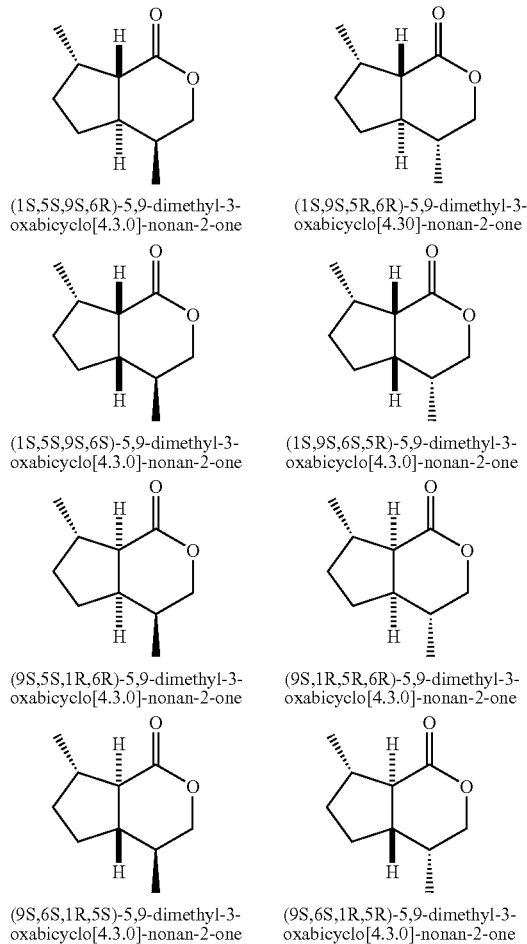

A "dihydronepetalactone" (DHN) will be understood to encompass any and all dihydronepetalactone stereoisomers and mixtures thereof, unless a particular isomer or mixture is specified. When dihydronepetalactone is prepared from a naturally occurring source of nepetalactone some variation in molar concentration of stereoisomers is expected. Preparation from a naturally occurring source is, however, a preferred method of preparation.

Regnier et al, op.cit., discloses the preparation of DHN from nepetalactone by the catalyzed hydrogenation of nepetalactone isolated from the essential oils of plants of the genus *Nepeta* (catmints). One preferred and convenient method for synthesis of dihydronepetalactone is thus by hydrogenation of nepetalactone obtained in relatively pure form from the essential oils isolated by various means from plants of the genus *Nepeta* (catmints). Catalysts such as platinum oxide and palladium supported on strontium carbonate give dihydronepalactone in 24-90% yields (Regnier et al. op.cit.). A particularly preferred method is described in U.S. application Ser. No. 10/405,444, filed Apr. 2, 2003, which is incorporated in its entirety as a part hereof for all purposes. Methods for isolation of essential oils are well known in the art, and examples of methodology for oil extraction include (but are not limited to) steam distillation, organic solvent extraction, microwave-assisted organic solvent extraction, supercritical fluid extraction, mechanical extraction and enfleurage (initial cold extraction into fats followed by organic solvent extraction).

The essential oils isolated from different *Nepeta* species are well known to possess different proportions of each naturally-occurring stereoisomer of nepetalactone (Regnier et al. op. cit.; DePooter, et al. op.cit.; Handjieva et al op.cit.). Thus DHN prepared from oil derived from any *Nepeta* species will necessarily be a mixture of stereoisomers thereof, the constitution of that mixture depending upon the particular species of *Nepeta* from which it is derived.

As discussed herein above, four chiral centers are present within the methylcyclopentanoid backbone of the nepetalactone at carbons 4, 4a, 7 and 7a as shown:

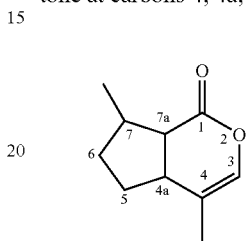

A total of eight pairs of dihydronepetalactone enantiomers are possible after hydrogenation of nepetalactone. Of these, the naturally occurring stereoisomers described thus far are (9S)-dihydronepetalactones. Preferred repellent materials in accordance with the present invention include a mixture of any or all of the possible stereoisomers of dihydronepetalactone. More preferred repellent materials include a mixture of (9S)-dihydronepetalactones. Most preferred are (9S)-dihydronepetalactone stereoisomers derived from (7S)-nepetalactones. This includes the compounds commonly known as cis,trans-nepetalactone, cis,cis-nepetalactone, trans,cis-nepetalactone, and trans,trans-nepetalactone, as illustrated in FIG. 1. The predominant stereoisomers produced by *N. cataria* (cis,trans and trans,cis-) are preferred.

Upon completion of the hydrogenation reaction, the resulting mixture of isomer products may be separated by a conventional method (e.g., preparative liquid chromatography) to yield each highly purified pair of dihydronepetalactone diastereomers. This permits the use of various different diastereomers as are found to be most effective against particular insects. It is preferable to isolate a specific nepetalactone isomer from a plant to convert to its corresponding pair of diastereomers by hydrogenation.

In addition to variation in nepetalactone stereoisomer content between different *Nepeta* species, intra-species variation is also known to exist. Plants of a given species may produce oils with different compositions depending on the conditions of their growth or growth stage at harvest. In fact variation in oil composition independent of growth conditions or growth stage at harvest has been found in *Nepeta racemosa*, (Clark, L. J., et al. op.cit). Plants of a single species exhibiting different oil compositions are termed chemotypes. In *Nepeta racemosa*, chemotypes exhibiting marked differences in the proportion of different nepetalactone stereoisomers exist. Thus, the preferred process for producing specific dihydronepetalactone enantiomers is hydrogenation of an oil from a *Nepeta chemotype* known to contain specific nepetalactone stereoisomers.

An insect as repelled by the composition of this invention includes any member of a large group of invertebrate animals characterized, in the adult state (non-adult insect states include larva and pupa), by division of the body into head, thorax, and abdomen, three pairs of legs, and, often (but not always) two pairs of membranous wings. This definition therefore includes but is not limited to a variety of biting insects (e.g., ants, bees, black flies, chiggers, fleas, green head flies, mosquitoes, stable flies, ticks, wasps), wood-boring insects (e.g., termites), noxious insects (e.g., houseflies, cockroaches, lice, roaches, wood lice), and household pests (e.g., flour and bean beetles, dust mites, moths, silverfish, weevils). In one embodiment, for example, the DHN compositions of the present invention are effective insect repellents against a wide spectra of common insect pests, such as those mentioned above and also including biting insects, wood-boring insects, noxious insects, and household pests, most particularly mosquitoes, stable flies, and ticks such as deer ticks.

In a further embodiment the DHN compositions of this invention are effective to repel any one or more of the members of the group consisting of bees, black flies, chiggers, fleas, green head flies, mosquitoes, stable flies, ticks, wasps, wood-boring insects, houseflies, cockroaches, lice, roaches, wood lice, flour and bean beetles, dust mites, moths, silverfish, and weevils. The insects repelled may also, however, be one or more those that are selected from a subgroup of the foregoing formed by omitting any one or more members from the whole group as set forth in the list in the first sentence of this paragraph. As a result, the repelled insect(s) may in such instance not only be those selected from any subgroup of any size that may be formed from the whole group as set forth in the list above, but may exclude the members that have been omitted from the whole group to form the subgroup. The subgroup formed by omitting various members from the whole group in the list above may, moreover, be an individual member of the whole group such that the repelled insect excludes all other members of the whole group.

A host is any plant or animal affected by insects. Typically, hosts are considered to be insect-acceptable food sources or insect-acceptable habitats. Hosts can be animals (including without limitation pets and/or other domesticated animals), humans, plants or a so-called "insect susceptible article", encompassing any inanimate article which is affected by insects. This may include buildings, furniture, and the like.

In a further embodiment of the present invention, DHN is incorporated into a host such as an insect susceptible article to produce an insect repellent article for the purpose either of deterring insects from landing on the article, or from occupying the air surrounding the article. Contemplated in this embodiment are those instances in which an article may already exhibit some degree of insect repellency prior to treatment with a DHN composition of the invention. In such instances it is contemplated that the insect repellency of the article will be enhanced by the application of the DHN composition of the invention.

An insect repellent is any compound or composition which deters insects from a host. It will be appreciated that such usage makes no distinction among compounds that have highly ephemeral effects as compared to those that exhibit long term beneficial effects, and/or those that require very high surface concentrations before there is an observable effect on insect behavior.

The term "insect repellent" thus indicates a compound or composition conferring on a host protection from insects when compared to no treatment at all. "Protection" desirably results in a statistically significant reduction in numbers of insects, and may, for example, be usefully determined by measuring mean complete protection time ("CPT") in tests in which insect behavior toward treated animals, including humans, and treated inanimate surfaces is observed. Mean CPT refers to the mean length of time over repetitions of tests in which the time before the first landing, probing or biting (in the case of a biting insect) or crawling (in the case of a crawling insect such as a tick or chigger) on a treated surface is observed [see e.g. US EPA Office of Prevention, Pesticides and Toxic Substances product performance test guidelines OPPTS 810.3700; and Fradin, M. S., Day, J. F. (2002) New England Journal of Medicine 347, 13-18]. In one exemplary embodiment of this invention, the insect repellent composition hereof has a mean CPT that is statistically indistinguishable from that of DEET. In the test in which this condition of the respective mean CPT performances of a DHN composition and DEET are shown to be statistically indistinguishable, the test conditions (including amounts of active ingredients) utilized must of course be identical, or, if not identical, must differ only in ways that do not prevent utilization of the results for the purposes of documenting the existence of the condition described.

As noted above, DHN compared favorably in performance with DEET. Moreover, DHN is advantageously prepared from naturally occurring nepetalactone derived from plants whereas DEET, and many other insect repellents, are not prepared from natural sources—an important consumer consideration when choosing an effective repellent. Preparation from natural sources also offers the potential for low production costs.

It is a particularly surprising aspect of the present invention that DHN provides a considerable improvement over the odor of DEET while exhibiting effective insect repellency. The DHN compounds and compositions of this invention possess a pleasant fragrance. The fragrance notes of the DHN materials make them useful in imparting, altering, augmenting or enhancing the overall olfactory component of an insect repellent composition or article, for example, by utilizing or moderating the olfactory reaction contributed by one or more other ingredients in the composition. Specifically, the DHN compositions of the invention may be utilized to either mask or modify the odor contributed by other ingredients in the formulation of the final repellent composition or article, and/or to enhance consumer appeal of a product by imparting a characteristic perfume or aroma.

It will be appreciated that the effectiveness of DHN or any insect repellent depends upon the surface concentration of the active ingredient on the host surface to which it is applied. Many compounds known in the art to exhibit insect repellency do so, however, only in relatively concentrated form. See, for example, McGovern et al in U.S. Pat. No. 4,416,881, which discloses the use of repellent concentrations of 6.25-25%. In other situations representative of the art, it is often found that concentrations of DEET much below 1% require repeated application to achieve an effective surface concentration, yet concentrations above 30% result in excessive surface concentration, which is both wasteful and conducive to the production of undesirable side effects. A further advantage of this invention is consequently that DHN not only provides effective insect repellency at concentrations similar to those employed for DEET, DHN may be employed at concentrations up to and including neat DHN (i.e. the composition hereof may, if desired, contain 100% by weight DHN). The property of effective repellency in DHN provides many options for economical utilization of the DHN active ingredient over a wide range of levels of concentration.

In one embodiment of the present invention, DHN is incorporated in effective amounts into a composition suitable for application to a host plant or animal, preferably to human skin. Suitable compositions include DHN and a vehicle, preferably alcohol such as iso-propyl alcohol, a lotion such as numerous skin creams such as are known in the art, or a siliceous clay. Preferably the DHN is present in the insect repellent composition of the invention at a concentration of about 0.1% to 30% by weight, preferably about 0.5% to 20% by weight, and most preferably about 1% to 15% by weight.

For an insect repellent to be effective the evaporation rate of the active ingredient from the host's skin or the treated article must be sufficiently high to provide a vapor density which has the desired effect on the target insects. However, a balance must be struck between evaporation rate and the desired duration of the insect repellent effect—too high an evaporation rate will deplete the insect repellent on the surface causing a loss in efficacy. Numerous extrinsic factors affect the evaporation rate, such as the ambient temperature, the temperature of the treated surface, and the presence or absence of air movement. The composition of this invention has a skin surface evaporation rate of at least a minimum effective evaporation rate, and preferably has a skin surface evaporation rate of at least a minimum effective evaporation rate for at least five hours.

In most cases, penetration into and through the skin is an undesirable mode of loss of compound from the skin surface. For example, insect repellents are known to be absorbed into human skin, making potential toxicity a concern on the one hand, and clearly removing the absorbed amount of repellent from insect repellent activity. Similar considerations must be made for insect repellent articles.

While DHN provides effective insect repellency under typical conditions of use, it may under some circumstances be desirable to reduce the rate of evaporation thereof. A variety of strategies may be employed to reduce the evaporation rate of DHN if so desired. For example, one method is to combine the DHN with a polymer or other inert ingredient, forcing the DHN to migrate through the mixture to the surface thereof before it can evaporate. However, if the result is dilution of the concentration of DHN that can be applied to the host's skin surface or that is present on the surface of an insect repellent article, thus reducing the overall potency of the formulation, this must be factored into the evaporation strategy selected. Alternatively, the active ingredient is micro-encapsulated to control rates of loss from the host's skin surface or insect repellent article. In still another alternative, a precursor molecule may be prepared, which slowly disintegrates on the skin surface or insect repellent article to release the active ingredient.

For example, release of the active ingredient may be, for example, by sub-micron encapsulation, in which the active ingredient is encapsulated (surrounded) within a skin nourishing protein just the way air is captured within a balloon. The protein may be used at, for example, a 20% concentration. An application of repellent contains many of these protein capsules that are suspended in either a water-based lotion, or water for spray application. After contact with skin the protein capsules begin to breakdown releasing the encapsulated dihydronepetalactone. The process continues as each microscopic capsule is depleted then replaced in succession by a new capsule that contacts the skin and releases its active ingredient. The process may take up to 24 hours for one application. Because a protein's adherence to the skin is so effective, these formulas are very resistant to perspiration (sweat-off), and water. When applied they are dry and comfortable with no greasiness. This system results in very effective protection, but it is only effective when used on skin because clothing does not have the capability to release the proteins. An alternative system uses a polymer to encase the repellent, which slows down early evaporation leaving more dihydronepetalactone available for later evaporation. This system can often increase a repellent's length of effectiveness by 25% to 50% over comparable non-entrapped products, but often feels greasy because of the presence of the polymer. In another alternative, a synergist is used to keep stimulating the evaporation of the dihydronepetalactone in the composition.

In the present invention, a variety of carriers or diluents for the above-disclosed dihydronepetalactones can be used. The carrier allows the formulation to be adjusted to an effective concentration of repellant molecules. When formulating a topical insect repellent suitable for human or animal skin, preferably, the repellant molecules are mixed in a dermatologically acceptable carrier. The carrier may further provide water repellency, prevent skin irritation, and/or soothe and condition skin. Factors to consider when selecting a carrier(s) for any formulation of insect repellent include commercial availability, cost, repellency, evaporation rate, odor, and stability. Some carriers can themselves have repellent properties. The carrier, moreover, should preferably also be one that will not be harmful to the environment.

Suitable for the present invention are one or more commercially available organic and inorganic liquid, solid, or semi-solid carriers or carrier formulations known in the art for formulating insect repellent products. For example the carrier may include silicone, petrolatum, or lanolin.

Examples of organic liquid carriers include liquid aliphatic hydrocarbons (e.g., pentane, hexane, heptane, nonane, decane and their analogs) and liquid aromatic hydrocarbons. Examples of other liquid hydrocarbons include oils produced by the distillation of coal and the distillation of various types and grades of petrochemical stocks, including kerosene oils that are obtained by fractional distillation of petroleum. Other petroleum oils include those generally referred to as agricultural spray oils (e.g., the so-called light and medium spray oils, consisting of middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid carriers can include liquid terpene hydrocarbons and terpene alcohols such as alpha-pinene, dipentene, terpineol, and the like.

Other carriers include aliphatic and aromatic alcohols, esters, aldehydes, ketones, mineral oil, higher alcohols, finely divided organic and inorganic solid materials. In addition to the above-mentioned liquid hydrocarbons, the carrier can contain conventional emulsifying agents which can be used for causing the dihydronepetalactone compounds to be dispersed in, and diluted with, water for end-use application.

Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Additionally, conventional or so-called "stabilizers" (e.g., tert-butyl sulfinyl dimethyl dithiocarbonate) can be used in conjunction with, or as a component of, the carrier or carriers comprising the compositions of the present invention.

Solid carriers that can be used in the compositions of the present invention include finely divided organic and inorganic solid materials. Suitable finely divided solid inorganic carriers include siliceous minerals such as synthetic and natural clay, bentonite, attapulgite, fuller's earth, diatomaceous earth, kaolin, mica, talc, finely divided quartz, and the like, as well as synthetically prepared siliceous materials, such as silica aerogels and precipitated and fume silicas. Examples of finely divided solid organic materials include cellulose, sawdust, synthetic organic polymers, and the like. Examples of semi-solid or colloidal carriers include waxy solids, gels (such as petroleum jelly), lanolin, and the like, and mixtures of well-known liquid and solid substances which can provide semi-solid carrier products, for providing effective repellency within the scope of the instant invention.

Insect repellent compositions of the present invention containing the dihydronepetalactones may also contain adjuvants known in the art of personal care product formulations, such as thickeners, buffering agents, chelating agents, preservatives, fragrances, antioxidants, gelling agents, stabilizers, surfactants, emolients, coloring agents, aloe vera, waxes, other penetration enhancers and mixtures thereof, and therapeutically or cosmetically active agents.

Therapeutically or cosmetically active ingredients useful in the compositions of the invention include fungicides, sunscreening agents, sunblocking agents, vitamins, tanning agents, plant extracts, anti-inflammatory agents, anti-oxidants, radical scavenging agents, retinoids, alpha-hydroxy acids, emolients, antiseptics, antibiotics, antibacterial agents or antihistamines, and may be present in an amount effective for achieving the therapeutic or cosmetic result desired.

The composition of this invention may also be blended with a non-dihydronepetalactone insect repellent, such as those included in the consisting of: benzil, benzyl benzoate, 2,3,4,5-bis(butyl-2-ene) tetrahydrofurfural, butoxypolypropylene glycol, N-butylacetanilide, normal-butyl-6,6-dimethyl-5,6-dihydro-1,4-pyrone-2-carboxylate, dibutyl adipate, dibutyl phthalate, di-normal-butyl succinate, N,N-diethyl-meta-toluamide, dimethyl carbate, dimethyl phthalate, 2-ethyl-2-butyl-1,3-propanediol, 2-ethyl-1,3-hexanediol, di-normal-propyl isocinchomeronate, 2-phenylcyclohexanol, p-methane-3,8-diol, and normal-propyl N,N-diethylsuccinamate.

The DHN composition of the invention may include any number of the above recited adjuvants in order to meet the requirements of any particular application. The specific proportions of each ingredient will similarly be dictated by the requirements of the application. However, the compositions of the invention should preferably comprise at least about 0.001% by weight DHN, or about 0.001% to about 80% by weight DHN, or about 0.01% to about 30% by weight of DHN, or about 0.1% to about 30% by weight of DHN, preferably about 0.5% to about 20% by weight, most preferably about 1% to about 15% by weight. In general, the composition of the repellent should contain sufficient amounts of active insect repellant material to be efficacious in repelling the insect from the host over a prolonged period of time (preferably, for a period of at least several hours).

Dihydronepetalactones may be utilized in the present invention in the form of individual diastereomers or a mixture of various diastereomers, or combined with other insect repellents. DHN may be employed at any concentration level suitable for the particular need, including neat. However, it is contemplated that the amount of DHN in an insect repellent composition or repellent article in accordance with the present invention will generally not exceed about 80% by weight.

The compositions of the invention may be formulated and packaged so as to deliver the product in a variety of forms including as a solution, suspension, cream, ointment, gel, film or spray, depending on the preferred method of use. The carrier may be an aerosol composition adapted to disperse the dihydronepetalactone into the atmosphere by means of a compressed gas.

Desirable properties of a topical insect repellent article include low toxicity, resistance to loss by water immersion or sweating, low or no odor or at least a pleasant odor, ease of application, and rapid formation of a dry tack-free surface film on the host's skin. In order to obtain these properties, the formulation for a topical insect repellent article should permit insect-infested animals (e.g., dogs with fleas, poultry with lice, cows with ticks, and humans) to be treated with an insect repellent composition of the present invention by contacting the skin, fur or feathers of such an animal with an effective amount of the repellent article for repelling the insect from the animal host. Thus, dispersing the article into the air or dispersing the composition as a liquid mist or fine dust will permit the repellent composition to fall on the desired host surfaces. Likewise, directly spreading of liquid/semi-solid/solid repellent article on the host is an effective method of contacting the surface of the host with an effective amount of the repellent composition.

Particularly because of the pleasant aroma associated with DHN, a further embodiment of the present invention is the incorporation of DHN into products which are not primarily associated with insect repellency in order to provide an effective degree of repellency thereto. Included among such products (but not thereto limited) are colognes, lotions, sprays, creams, gels, ointments, bath and shower gels, foam products (e.g., shaving foams), makeup, deodorants, shampoo, hair lacquers/hair rinses, and personal soap compositions (e.g., hand soaps and bath/shower soaps).

Further contemplated in the present invention are those embodiments wherein DHN provides effective insect repellency in a variety of articles that are susceptible to attack by insects by incorporation therein. In a typical embodiment the articles are outdoors, but need not be. Among the articles contemplated are included, but not limited to, air fresheners, candles, various scented articles, fibers, sheets, textile goods, paper, paint, ink, clay, wood, furniture (e.g., for patios and decks), carpets, sanitary goods, plastics, polymers, and the like.

In one embodiment, the dihydronepetalactone is combined with a polymer to provide moldability, reduction of evaporation rate, and controlled release. Such a polymer may be biodegradeable Suitable polymers include but are not limited to high density polyethylene, low density polyethylene, biodegradable thermoplastic polyurethanes, biodegradable ethylene polymers, and poly(epsilon caprolactone) homopolymers and compositions containing the same, as disclosed for example in U.S. Pat. No. 4,496,467, U.S. Pat. No. 4,469,613 and U.S. Pat. No. 4,548,764. Preferred biodegradeable polymers include DuPont Biomax® biodegradeable polyester and poly-L-lactide.

This invention also involves a process for manufacturing DHN in which a palladium catalyst is used. The term "catalyst" as used herein refers to a substance that affects the rate of a chemical reaction (but not the reaction equilibrium) and emerges from the process chemically unchanged.

The process for the production of a dihydronepetalactone of formula (XVI) involves hydrogenating a nepetalactone of formula (XV) according to the following scheme:

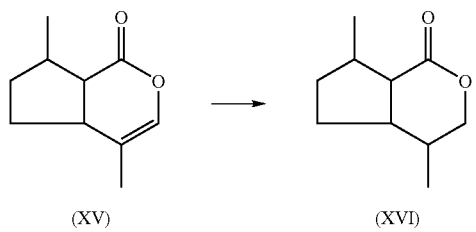

(XV)   (XVI)

in the presence of palladium supported on a catalyst support that is not SrCO$_3$.

The term "promoter" as used herein is a compound that is added to enhance the physical or chemical function of a catalyst. A chemical promoter generally augments the activity of a catalyst and may be incorporated into the catalyst during any step in the chemical processing of the catalyst constituent. The chemical promoter generally enhances the physical or chemical function of the catalyst agent, but can also be added to retard undesirable side reactions. A "metal promoter" refers to a metallic compound that is added to enhance the physical or chemical function of a catalyst.

Hydrogenation of nepetalactone is effected in the presence of a suitable active metal hydrogenation catalyst. Acceptable solvents, catalysts, apparatus, and procedures for hydrogenation in general can be found in Augustine, *Heterogeneous Catalysis for the Synthetic Chemist*, Marcel Decker, New York, N.Y. (1996). Many hydrogenation catalysts are effective, including (without limitation) those containing as the principal component iridium, palladium, rhodium, nickel, ruthenium, platinum, rhenium, compounds thereof, combinations thereof, and the supported versions thereof.

The metal catalyst used in the process of this invention may be used as a supported or as an unsupported catalyst. A supported catalyst is one in which the active catalyst agent is deposited on a support material by spraying, soaking or physical mixing, followed by drying, calcination, and if necessary, activation through methods such as reduction or oxidation. Materials frequently used as support are porous solids with high total surface areas (external and internal) which can provide high concentrations of active sites per unit weight of catalyst. The catalyst support may enhance the function of the catalyst agent; and supported catalysts are generally preferred because the active metal catalyst is used more efficiently. A catalyst which is not supported on a catalyst support material is an unsupported catalyst.

The catalyst support can be any solid, inert substance including, but not limited to, oxides such as silica, alumina, titania, calcium carbonate, barium sulfate, and carbons. The catalyst support can be in the form of powder, granules, pellets, or the like. A preferred support material of the present invention is selected from the group consisting of carbon, alumina, silica, silica-alumina, titania, titania-alumina, titania-silica, barium, calcium, compounds thereof and combinations thereof. Suitable supports include carbon, SiO$_2$, CaCO$_3$, BaSO$_4$ and Al$_2$O$_3$. Moreover, supported catalytic metals may have the same supporting material or different supporting materials.

In one embodiment of the instant invention, a more preferred support is carbon. Further preferred supports are those, particularly carbon, that have a surface area greater than 100-200 m$^2$/g. Further preferred supports are those, particularly carbon, that have a surface area of at least 300 m$^2$/g.

Commercially available carbons which may be used in this invention include those sold under the following trademarks: Barneby & Sutcliffe™, Darco™, Nuchar™, Columbia JXN™, Columbia LCK™, Calgon PCB™, Calgon BPL™, Westvaco™, Norit™ and Barnaby Cheny NB™. The carbon can also be commercially available carbon such as Calsicat C, Sibunit C, or Calgon C (commercially available under the registered trademark Centaur®).

Preferred combinations of catalytic metal and support system include palladium on carbon such as in ESCAT#142 catalyst (Englehart).

While the weight percent of catalyst on the support is not critical, it will be appreciated that the higher the weight percent of metal, the faster the reaction. A preferred content range of the metal in a supported catalyst is from about 0.1 wt % to about 20 wt % of the whole of the supported catalyst (catalyst weight plus the support weight). A more preferred catalytic metal content range is from about 1 wt % to about 10 wt % by weight of the whole of the supported catalyst. A further preferred catalytic metal content range is from about 3 wt % to about 7 wt % by weight of the whole of the supported catalyst.

Optionally, a metal promoter may be used with the catalytic metal in the method of the present invention. Suitable metal promoters include: 1) those elements from groups 1 and 2 of the periodic table; 2) tin, copper, gold, silver, and combinations thereof; and 3) combinations of group 8 metals of the periodic table in lesser amounts.

Temperature, solvent, catalyst, pressure and mixing rate are all parameters that affect the hydrogenation. The relationships among these parameters may be adjusted to effect the desired conversion, reaction rate, and selectivity in the reaction of the process.

Within the context of the present invention the preferred temperature is from about 25° C. to 250° C., more preferably from about 50° C. to about 150° C., and most preferred from about 50° C. to 100° C. The hydrogen pressure is preferably about 0.1 to about 20 MPa, more preferably about 0.3 to 10 MPa, and most preferably about 0.3 to 4 MPa. The reaction may be performed neat or in the presence of a solvent. Useful solvents include those known in the art of hydrogenation such as hydrocarbons, ethers, and alcohols. Alcohols are most preferred, particularly lower alkanols such as methanol, ethanol, propanol, butanol, and pentanol. Where the reaction is carried out according to the preferred embodiments, selectivites in the range of at least 70% are attainable where selectivites of at least 85% are typical. Selectivity is the weight percent of the converted material that is dihydronepetalactone where the converted material is the portion of the starting material that participates in the hydrogenation reaction.

The process of the present invention may be carried out in batch, sequential batch (i.e. a series of batch reactors) or in continuous mode in any of the equipment customarily employed for continuous processes (see, for example, H. S. Fogler, *Elementary Chemical Reaction Engineering*, Prentice-Hall, Inc., NJ, USA). The condensate water formed as the product of the reaction is removed by separation methods customarily employed for such separations.

Upon completion of the hydrogenation reaction, the resulting mixture of dihydronepetalactone isomer products may be separated by a conventional method, such as for example, by distillation, by crystallization, or by preparative liquid chromatography to yield each highly purified pair of dihydronepetalactone enantiomers. Chiral chromatography may be employed to separate enantiomers.

The present invention is further described in but not limited by the following specific embodiments.

EXAMPLES

In the following examples, the notation "w/v" refers to the weight in grams of the active ingredient per 100 mL of solution.

Other abbreviations employed are as follows: "h" means hour(s), "min" means minute(s), "sec" means second(s), "d" means day(s), "mL" means milliliters, "L" means liters, "m/z" means mass (m) to charge (z) ratio, "ppm" means parts per million, "mol %" means percentage expressed on a molar basis, "Hz" means Hertz (1/sec), and "psig" means pounds per square inch guage.

Example 1

Preparation of Nepetalactones by Fractional Steam Distillation of Oil of *Nepeta Cataria*

A sample of commercially-available catnip oil, prepared by steam distillation of herbaceous material from the catmint *Nepeta cataria*, was obtained (Berjé, Bloomfield, N.J., USA). Combined gas chromatography—mass spectrometry (GC-MS) of the oil as received indicated that the principal constituents were nepetalactone stereoisomers (FIG. 1). However, as purchased, the oil is a highly contaminated natural product, and it is desirable to refine the extract to a purified nepetalactone. We fractionally distilled to remove contaminants with higher and lower boiling points than the nepetalactones.

Thus the nepetalactone fraction was prepared by fractional distillation of the as-received oil (2 l pot; 12 in.×1 in. packed column with 0.24" SS packing; variable reflux head; ca. 2 mm Hg, with fractions collected between 80° C. and 99° C.). FIG. 2A presents the GC-MS total ion chromatogram of the nepetalactone-enriched fraction prepared by fractional distillation of the commercial sample of *Nepeta cataria* essential oil. The conditions employed were: column HP5-MS, 25 m×0.2 mm; oven 120° C., 2 min, 15° C./min, 210° C., 5 min.; He @ 1 ml/min. Peaks with m/z 166 are nepetalactones; the unlabelled peaks correspond to minor sesquiterpenoid contaminants.

In FIG. 3A, the mass spectrum of the major peak (6.03 min, nepetalactone) in FIG. 2A is shown. $^1H$ and $^{13}C$ NMR analysis of the oil and the purified material was also carried out, and the $^{13}C$ data is presented (FIG. 4). The $^{13}C$ chemical shifts for the four possible stereoisomers reported in the literature were compared to the spectra taken for the sample. Three stereoisomers were detected and the amounts were quantified based on the carbonyl region at around 170 ppm. The chemical shifts, for both the original oil and the enriched material, are provided in Table 1. Each carbon atom of nepetalactone is identified, as shown in FIG. 4.

TABLE 1

$^{13}C$ Chemical Shifts and Mol % Values of Nepetalactone Stereoisomers Present in Commercial Sample of Essential Oil of Catmint (*Nepeta cataria*) and in Fraction Purified by Steam Distillation

| | ESSENTIAL OIL | | | PURIFIED FRACTION | | |
| --- | --- | --- | --- | --- | --- | --- |
| ATOM | cis, trans- δ (ppm) | trans, cis- δ (ppm) | cis, cis- δ (ppm) | cis, trans- δ (ppm) | trans, cis- δ (ppm) | Cis, cis- δ (ppm) |
| a | 170.9 | 170.1 | | 170.8 | 170.1 | |
| b | 133.7 | 135.9 | 134.2 | 133.7 | 135.9 | 134.2 |
| c | 115.3 | 120.4 | | 115.3 | 120.4 | |
| d | 40.8 | 37.3 | 39.6 | 40.8 | 37.4 | 39.5 |
| e | 49.4 | 49.1 | 46.4 | 49.5 | 49.1 | 46.3 |
| f | 39.7 | 32.1 | 38.4 | 39.8 | 32.1 | 38.4 |
| g | 33.0 | 30.0 | 32.7 | 33.1 | 30.0 | 32.7 |
| h | 30.9 | 26.1 | 30.4 | 31.0 | 26.1 | 30.5 |
| j | 20.2 | 17.5 | 17.1 | 20.3 | 17.6 | 17.2 |
| i | 15.4 | 14.2 | 14.7 | 15.5 | 14.2 | 14.8 |
| Mol % | 80.20% | 17.70% | 2.10% | 84.50% | 14.30% | 1.20% |

This analysis indicated that in the oil, nepetalactones were present in the following proportions: 80.2 mol % cis,trans-nepetalactone, 17.7 mol % trans,cis-nepetalactone and 2.1 mol % cis,cis-nepetalactone. The data indicated the proportions of nepetalactones in the purified material were 84.5 mol % cis,trans-nepetalactone, 14.3 mol % trans,cis-nepetalactone and 1.2 mol % cis,cis-nepetalactone. GC-MS analysis of this purified fraction indicated that it consisted predominantly of these nepetalactones (m/z 166), accompanied by trace amounts of the sesquiterpenoids caryophyllene and humulene (data not shown).

Example 2

Preparation of Dihydronepetalactones 107 g of the distilled nepetalactone fraction of the catmint oil prepared as described in Example 1 was dissolved in ethanol (200 ml) and placed in a Fisher-Porter bottle with 12.7 g 2% $Pd/SrCO_3$ (Aldrich 41,461-1) as catalyst. The tube was evacuated and backfilled with $H_2$ twice, then charged with $H_2$ at 30 psig. After 48 h stirring at room temperature, the tube was vented and the contents filtered over Celite to remove catalyst. The solvent was removed under vacuum, yielding a clear oil.

GC-MS analysis (column HP5-MS, 25 m×0.2 mm; Oven 120° C., 2 min, 15° C./min, 210° C., 5 min.; He @ 1 ml/min) was conducted on this material. The total ion chromatogram is presented in FIG. 2B. This analysis indicated that the principal component (65.43% area; Rt 7.08 min) represented a dihydronepetalactone isomer, with m/z 168; the mass spectrum of this component is presented in FIG. 3B. This spectrum contains an ion with m/z 113, diagnostic for dihydronepetalactones (Jefson, M., et al. op.cit.). Five additional peaks, representing the remaining dihydronepetalactone diastereomers which might be derived from the three nepetalactones present in the starting material were also represented in the chromatogram. These occurred at Rt 5.41 min, 6.8% area, m/z 168; Rt 5.93 min, area 1.2%, m/z 168; Rt 6.52 min, 4.88% area, mass 168; Rt 6.76 min, 13.8% area, m/z 168 and Rt 7.13 min, 1.25% area, m/z 168. No residual nepetalactones were detected by GC-MS.

$^{1}$H, $^{13}$C and a series of 2D NMR analyses were also performed. The carbonyl region of the $^{13}$C NMR spectrum (FIG. 5) showed at least five spin systems, one of them in larger amounts than the other four (ca. 75%). Very little residual nepetalactone was detected.

Based on the analysis of coupling constants and the intensities of the different NOE cross peaks observed, the stereochemistry of the principal component of the material was determined to be the

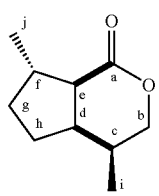

Formula 2 dihydronepetalactone of Formula 2 (9S, 5S, 1R, 6R)-5,9-dimethyl-3-oxabicyclo[4.3.0]nonan-2-one).

dihydronepetalactone of Formula 2 (9S,5S,1R,6R)-5,9-dimethyl-3-oxabicyclo[4.3.0]nonan-2-one).

The distance between the methyl group (i) and proton (d) is longer than the distance between the methyl group 0) and the proton (e), an observation consistent with the cis-trans stereochemical configuration.

The stereoisomer isodihydronepetalactone (9S,5R, 1R,6R)-5,9-dimethyl-3-oxabicyclo[4.3.0]nonan-2-one; (Formula 3) was similarly identified by $^{13}$C chemical shifts and is present in 3.6%.

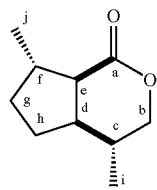

Formula 3

Thus the GC-MS and NMR data indicate that hydrogenation of the mixture of nepetalactone stereoisomers yielded the corresponding dihydronepetalactone diastereomers, as expected. The pair of diastereomers (Formula 2 and Formula 3) derived from cis,trans-nepetalactone (84.5 Mol % of the starting material) were the predominant dihydronepetalactones, at 78.6% of the mixture following hydrogenation.

Example 3

Repellency Testing of a Dihydronepetalactone Mixture

The DHN prepared in accordance with Example 2 (designated "mDHN") was evaluated for its repellent effects against female *Aedes aegypti* mosquitoes.

Approximately 250 female *Aedes aegypti* mosquitoes were introduced into a chamber containing 5 wells, each covered by a Baudruche (animal intestine) membrane. Wells were filled with bovine blood, containing sodium citrate (to prevent clotting) and ATP (72 mg ATP disodium salt per 26 ml of blood), and heated to 37° C. A volume of 25 µl of isopropyl alcohol, containing one of the test specimens shown in Table 2, was applied to each membrane.

TABLE 2

Experimental Design Applied for Repellency Testing

| Purpose | Compound | Concentration |
| --- | --- | --- |
| Untreated Control | Isopropyl alcohol | 100% |
| Positive Control | Isopropyl alcohol with DEET | 1.0% (w/v) |
| Experimental Samples | Isopropyl alcohol with Dihydronepetalactones | 1.0% (w/v) |
| | | 2.5% (w/v) |
| | | 5.0% (w/v) |

After 5 min, 4 day-old female mosquitoes were added to the chamber. The number of mosquitoes probing the membranes for each treatment was recorded at 2 min intervals over 20 min. Each datum represents the mean of three replicate experiments.

Table 3 presents the amount of time taken before the female *A. aegypti* mosquitoes first probed each treated membrane The numbers in parantheses are the standard error of the mean (SEM) for the three replicates.

TABLE 3

Effect of Dihydronepetalactone Concentration on Mean Time to "First Probe"

| Repellent Concentration | Mean Time (min) (SEM) |
| --- | --- |
| Isopropyl alcohol (untreated control) | 4.66 (0.66) |
| 1% DEET (positive control) | 12.0 (0.0) |
| 1% mDHN | 8.0 (1.15) |
| 2.5% mDHN | 9.33 (3.33) |
| 5% mDHN | 19.33 (0.66) |

Mosquitoes began probing the untreated control well within 4.6 min. Dihydronepetalactones at 5% concentration was found to discourage mosquito "first probing" for approximately 19 min, compared to 12 min for DEET (at 1% w/v). Lower concentrations of dihydronepetalactones (1% and 2.5% w/v) were found to inhibit first probing for an average of 8 and 9.3 min, respectively.

The distribution of landing/probing density by female *A. aegypti* on membranes treated with dihydronepetalactones was analyzed over time, and is shown graphically in FIG. 6. The total number of probes permitted on each membrane during the course of the experiments were determined, and the results are summarized in Table 4. DHN at 5% concentration was found to almost eliminate mosquito probes for 20 minutes; only a single probe was recorded over the entire 20 min test time, while DEET (1% w/v) permitted an average of 4.55 mosquitoes to land. Again, lower concentrations of DHN (1% and 2.5% w/v) were found to exhibit repellency (as compared to the untreated control), but at lower levels than the positive control (DEET at 1% w/v).

TABLE 4

Number of Probes Permitted According to Repellency Concentration

| Repellent Concentration | Mean Number of probes (SEM) |
| --- | --- |
| Isopropyl alcohol (untreated control) | 58.66 (4.48) |
| 1% DEET (positive control) | 4.55 (0.29) |
| 1% mDHN | 14.0 (6.8) |
| 2.5% mDHN | 6.33 (1.2) |
| 5% mDHN | 0.33 (0.33) |

Again, the data shows that at all concentrations tested dihydronepetalactones were repellent, although significantly increased repellency with respect to 1% DEET was observed only at 5% (w/v).

Example 4

Preparation of Dihydronepetalactones from trans,cis-nepetalactone

A number of plants were grown from seed of the catmint *Nepeta racemosa* (Chiltern Seeds, Cumbria, UK). Leaf pairs plucked from individual plants were immersed in ethyl acetate and after 2 h the solvent was removed and the extracts analyzed by gas chromatography. Plants producing preponderantly trans,cis-nepetalactone in their oils were thus identified (Clark, L. J., et al. op.cit.), and grown to maturity. Leaf material from these plants was harvested, freeze-dried, extracted into ethyl acetate, and the extracts concentrated. Nepetalactone was purified from the concentrated extract by silica gel chromatography in hexane/ethyl acetate (9:1) followed by preparative thin-layer chromatography on silica using the same solvent mixture. After removal of the solvent and re-dissolving in hexane, the trans,cis-nepetalactone was crystallized on dry ice. GC-MS and NMR ($^1$H and $^{13}$C) analysis confirmed the identity of the crystalline material as trans,cis-nepetalactone. The $^{13}$C chemical shifts (FIG. 7), compared to the chemical shifts of Table 1, are shown in Table 5.

TABLE 5

$^{13}$C chemical shifts of the nepetalactone sample prepared in Example 4, compared to the chemical shifts of trans, cis-nepetalactone (from TABLE 1)

| Atom | trans, cis-nepetalactone δ (ppm) | Sample δ (ppm) |
| --- | --- | --- |
| a | 170.1 | 170.3 |
| b | 135.9 | 136.0 |
| c | 120.4 | 120.5 |
| d | 37.3 | 37.5 |
| e | 49.1 | 49.3 |
| f | 32.1 | 32.2 |
| g | 30.0 | 30.1 |
| h | 26.1 | 26.3 |
| j | 17.5 | 17.7 |
| i | 14.2 | 14.4 |

Hydrogenation of the trans,cis-nepetalactone thus prepared was carried out in ethanol using ESCAT#142 catalyst (Englehart) at 50° C. for 4 h. GC-MS and NMR ($^1$H and $^{13}$C) confirmed that the trans,cis-nepetalactone had been quantitatively converted to the corresponding dihydronepetalactone stereoisomers, with one in significant excess. NMR analysis of the major diastereomer: $^1$H NMR (500 MHz, CDCl$_3$): d 0.97 (d, 3H, J=6.28 Hz), 0.98 (d, 3H, J=6.94 Hz) d 1.24 (m, 2H), 1.74 (m, 1H), 1.77 (m, 2H), 1.99 (m, 2H), 2.12 (dd, 1H, J=6.86 and 13.2 Hz), 2.51 (m, 1H), 3.78 (tr, 1H, J=11.1 Hz), 4.33 (dd, 1H, J=5.73 and 11.32 Hz); $^{13}$C (500 MHz, CDCl$_3$): d 15.43, 18.09, 27.95, 30.81, 31.58, 35.70, 42.51, 51.40, 76.18, 172.03. The $^{13}$C NMR spectrum (FIG. 8) indicated that this major diastereomer constituted ca. 93.7% of the preparation. Based on the observed couplings for the methylene to the lactone oxygen, the stereogenic methine carbon bearing methyl group, the methyl group itself and the bridgehead methine, it is concluded that the diastereomer is most likely the (1S,9S,5R,6R)-5,9-dimethyl-3-oxabicyclo[4.3.0]nonan-2-one) of Formula 4.

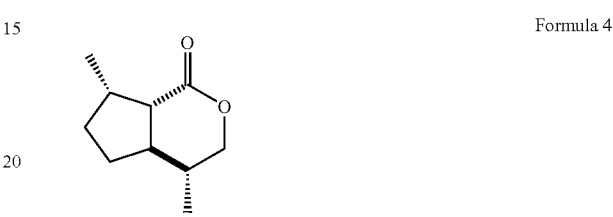

Formula 4

The magnitude of the observed couplings are consistent with dihedral angles between the protons on vicinal carbon atoms in the above structure according to the Karplus equation (ref. Spectrophotometric Identification of Organic Compounds, 4th. edition, Robert M. Silverstein, G. Clayton Bassler and Terence C. Morill, 1981, page 208-210).

Example 5

Repellency Testing of Dihydronepetalactones prepared by Hydrogenation of trans,cis-Nepetalactone The dihydronepetalactone prepared in Example 4, Formula 4, was tested for repellency against *Aedes aegypti* mosquitoes essentially as described in Example 3. The experimental design is summarized in Table 6, and all data presented is from five replicate experiments.

TABLE 6

Experimental Design Applied for Repellency Testing

| Purpose | Compound | Concentration |
| --- | --- | --- |
| Untreated Control | Isopropyl alcohol | 100% |
| Positive Control | Isopropyl alcohol with DEET | 1.0% (w/v) |
| Experimental Samples | Isopropyl alcohol with DHN | 1.0% (w/v) |
| | | 0.5% (w/v) |
| | | 0.2% (w/v) |

Table 7 presents the effect of DHN concentration with respect to the amount of time taken before the female *A. aegypti* mosquitoes first probed each membrane.

TABLE 7

Effect of Dihydronepetalactone Concentraton on Mean Time to "First probe"

| Repellent Concentration | Mean Time (min) (SEM) |
| --- | --- |
| Isopropyl alcohol (untreated control) | 8.0 (1.67) |
| 1% DEET (positive control) | 14.8 (3.2) |
| 1% DHN | 16.0 (2.09) |

TABLE 7-continued

Effect of Dihydronepetalactone Concentraton
on Mean Time to "First probe"

| Repellent Concentration | Mean Time (min) (SEM) |
|---|---|
| 0.5% DHN | 9.6 (2.48) |
| 0.2% DHN | 8.4 (1.16) |

Dihydronepetalactone at 1% concentration was found to discourage mosquito "first probing" for approximately 16 min. DEET at the same concentration, exhibited a mean time to first probe of 14.8 min. Lower concentrations of dihydronepetalactone (0.5% and 0.2% w/v) were found to inhibit first probing for an average of 9.6 and 8.4 min, respectively.

The distribution of probing density by female *A. aegypti* on membranes treated with dihydronepetalactones was analyzed over time, as shown graphically in FIG. 9. The total number of probes permitted on each membrane during the course of the experiments were determined, and the results are summarized in Table 8. DHN at 1.0% concentration was found to completely eliminate mosquito probing for 10 minutes, while DEET (1% w/v) permitted mosquitoes to initiate probing by 6 min. Again, lower concentrations of dihydronepetalactone (0.5% and 0.2% w/v) were found to exhibit repellency (as compared to the untreated control), but at lower levels than the positive control (DEET at 1% (w/v)).

TABLE 8

Number of Probes Permitted According to Repellent and
Concentration During 20 minute Observation Period

| Repellent Concentration | Mean Number of Probes (SEM) |
|---|---|
| Isopropyl alcohol (untreated control) | 41.4 (18.46) |
| 1% DEET (positive control) | 4.8 (3.2) |
| 1% DHN | 4.0 (2.16) |
| 0.5% DHN | 16.2 (5.49) |
| 0.2% DHN | 23.2 (5.97) |

Percentage repellency was calculated for each repellent treatment at each observation time using the following equation:

$$\% \text{ Repellency} = 100 - [(T/C) \times 100]$$

where:

$T$ = the mean number of mosquitoes probing a treated well for that replicate at time $t_x$ $C$ = the mean number of mosquitoes probing the IPA control well at time $t_x$ The resulting percentages were then arcsine transformed and an ANOVA was conducted using the calculated repellency from all five replicates. Multiple comparisons of means were conducted using the Student-Newman-Keuls test. The mean arcsines from ANOVA were then converted back into percentages. The results are shown in Table 9.

TABLE 9

Mean percentage repellencies as calculated from the ANOVA

| Repellent Treatment | Mean (%) |
|---|---|
| 1% DEET (positive control) | 92.4 |
| 1% DHN | 96.1 |

TABLE 9-continued

Mean percentage repellencies as calculated from the ANOVA

| Repellent Treatment | Mean (%) |
|---|---|
| 0.5% DHN | 66.7 |
| 0.2% mDHN | 62.5 |

1% DHN ranked first in repellency, and was statistically indistinguishable from 1% DEET.

Example 6

Repellency Testing of Dihydronepetalactones
Against Stable Flies (*Stomoxys calcitrans*)

DHN derived from hydrogenation of trans,cis-nepetalactone (consisting principally of 1S,9S,5R,6R-5,9-dimethyl-3-oxabicyclo[4.3.0]nonan-2-one; Formula 4), designated "Experimental Sample #1", and the mixture of dihydronepetalactones prepared according to Example 2 (designated Experimental Sample #2; mDHN), were tested for repellency against *Stomoxys calcitrans*, essentially as described in Example 3. The DHN used here differed from that prepared in Example 4 in that it was derived from hydrogenation (using a Pd/SrCO$_3$ catalyst) of trans,cis-nepetalactone crystallized from commercial oil (Berjé, N.J.). In these experiments, an additional positive control compound was included, namely p-menthane-3,8-diol (PMD), obtained from Takasago International Corp. (USA), Rockleigh, N.J. The experimental design is summarized in Table 10, and all data presented is an average of five replicate experiments.

TABLE 10

Experimental Design Applied for Repellency
Testing against Stable Flies

| Purpose | Compound | Concentration |
|---|---|---|
| Untreated Control | Isopropyl alcohol | 100% |
| Positive control #1 | Isopropyl alcohol with PMD | 1.0% (w/v) |
| Positive Control #2 | Isopropyl alcohol with DEET | 1.0% (w/v) |
| Experimental Sample #1 | Isopropyl alcohol with Dihydronepetalactone (DHN) | 1.0% (w/v) |
| Experimental Sample #2 | Isopropyl alcohol with Dihydronepetalactone diastereomer mix (mDHN) | 1.0% (w/v) |

In these tests, an accurate time to "first landing" could not be determined, since some landings occurred before the first exposure period of 2 min in three or more of the five replicates for each test variable.

The distribution of landing density by stable flies on membranes treated with dihydronepetalactones was analyzed over time, as shown graphically in FIG. 10. The total number of landings permitted on each membrane during the course of the experiments were determined, and the results are summarized in Table 11. Landings commenced on exposure of the insects to the test wells, and appeared to peak after ca. 5 min, gradually decreasing thereafter over time. Overall, the number of landings on membranes treated with dihydronepetalactones at 1% concentration were significantly fewer than observed on untreated (IPA) membranes, and equivalent to those observed with DEET (1% w/v). p-Menthane-3,8-diol (PMD) was less effective in repelling landings than either the dihydronepetalactones or DEET throughout the course of the experiment, and although some initial repellency could be observed, this compound became ineffective after 6 min. Again, this data indicates that 1% dihydronepetalactones exhibited equivalent repellent activity to 1% DEET.

TABLE 11

Number of Landings Permitted During 20 minute Test

| Repellent Treatment | Mean Number of Landings (SEM) |
|---|---|
| Isopropyl alcohol (untreated control) | 44.0 (8.59) |
| 1% PMD (positive control #1) | 33.6 (9.21) |
| 1% DEET (positive control #2) | 17.8 (4.96) |
| 1% DHN | 21.2 (3.35) |
| 1% mDHN | 18.8 (8.59) |

Percentage repellency and statistical analyses were carried out as described in Example 5, and the results presented in Table 12.

TABLE 12

Mean percentage repellencies as calculated from the ANOVA

| Repellent Treatment | Mean (%) |
|---|---|
| 1% PMD (positive control #1) | 4.7 |
| 1% DEET (positive control #2) | 55.5 |
| 1% DHN | 43.2 |
| 1% mDHN | 49.8 | mDHN, DEET and DHN performed statistically equally well, providing 43.2 to 55.5% repellency, and were statistically better than PMD, which gave only 4.7% repellency when compared to IPA.

Example 7

Repellency Testing of Dihydronepetalactones Against Anopheles Mosquitoes (*Anopheles albimanus*)

DHN derived from hydrogenation of trans,cis-nepetalactone (consisting principally of 1S,9S,5R,6R-5,9-dimethyl-3-oxabicyclo[4.3.0]nonan-2-one; Formula 4) designated "Experimental Sample #1", and the mixture of dihydronepetalactones prepared according to Example 2 (designated as "Experimental Sample #2"; mDHN) were tested for repellency against one hundred unfed adult female *A. albimanus*, essentially as described in Example 3. The DHN used here differed from that prepared in Example 4 in that it was derived from hydrogenation (using a Pd/SrCO$_3$ catalyst) of trans,cis-nepetalactone crystallized from commercial oil (Berjé, Bloomfield, N.J.). PMD was again included as a further control. The experimental design is summarized in Table 13, and all data presented is the average of five replicate experiments.

TABLE 13

Experimental Design Applied for Repellency Testing against *Anopheles* Mosquitoes

| Purpose | Compound | Concentration |
|---|---|---|
| Untreated Control | Isopropyl alcohol | 100% |
| Positive control #1 | Isopropyl alcohol with PMD | 1.0% (w/v) |
| Positive Control #2 | Isopropyl alcohol with DEET | 1.0% (w/v) |
| Experimental Sample #1 | Isopropyl alcohol with Dihydronepetalactone (DHN) | 1.0% (w/v) |
| Experimental Sample #2 | Isopropyl alcohol with Dihydronepetalactone diastereomer mix (mDHN) | 1.0% (w/v) |

In these tests, an accurate time to "first probing" could not be determined, since some probes occurred before the first exposure period of 2 min in two or more of the five replicates for each test variable. The distribution of probing density by anopheles mosquitoes on membranes treated with dihydronepetalactones was analyzed over time, as shown graphically in FIG. 11. Probing commenced on exposure of the insects to the test wells, and gradually increased thereafter over time. Overall, the number of probes on membranes treated with dihydronepetalactones at 1% concentration were significantly fewer than observed on untreated (IPA) membranes throughout the experiment.

The total number of probes permitted on each membrane during the course of the experiments were determined, and the results are summarized in Table 14. The data indicates that 1% dihydronepetalactones exhibited higher repellent activity compared to equivalent concentrations of either DEET or PMD against *A. albimanus*.

TABLE 14

Number of Landings Permitted During 20 minute Test

| Repellent Treatment | Mean Number of Probes (SEM) |
|---|---|
| Isopropyl alcohol (untreated control) | 66.2 (15.53) |
| 1% PMD (positive control #1) | 47.2 (8.57) |
| 1% DEET (positive control #2) | 50.4 (13.01) |
| 1% DHN | 38.0 (9.71) |
| 1% mDHN | 34.8 (6.26) |

Percentage repellency and statistical analyses were carried out as described in Example 5, and the results presented in Table 15.

TABLE 15

Mean percentage repellencies as calculated from the ANOVA

| Repellent Treatment | Mean (%) |
|---|---|
| 1% PMD (positive control #1) | 11.5 |
| 1% DEET (positive control #2) | 13.3 |
| 1% DHN | 32.9 |
| 1% mDHN | 46.1 | mDHN was statistically superior to DEET and provided 46.1% repellency. DHN, while statistically equal to mDHN, was also statistically equal to DEET and provided 32.9% repellency. DEET and PMD, which provided 13.3% and 11.5% repellency respectively, were statistically equal in efficacy.

Example 8

Repellency of Dihydronepetalactones Towards the Deer Tick, *Ixodes scapularis*

DHN derived from hydrogenation of trans,cis-nepetalactone (consisting principally of 1S,9S,5R,6R-5,9-dimethyl-3-oxabicyclo[4.3.0]nonan-2-one; Formula 4) prepared as in Example 7, and the mixture of dihydronepetalactones prepared according to Example 2 were tested for repellency against *I. Scapularis*, with DEET included in the test as a positive control.

A volume of 25 µl of each compound (30% (w/v) in isopropanol) was applied within 4 cm diameter circles drawn on the left forearms of six male human volunteers. Each volunteer had two repellents applied individually within two circles on this forearm; a single 4 cm diameter circle drawn on the other arm was left untreated to act as a control for tick attractiveness. Laboratory-reared unfed nymphs of the deer tick *Ixodes scapularis* were brought within 1 mm of the untreated circles on cotton buds (Q-tip®). If normal questing behavior was observed, and/or the insect crawled onto the untreated area, it was deemed qualified and then presented to a treated area. A qualified tick which quested at or crawled onto the treated area within 60 s was recorded as having not been repelled. A qualified tick which did not quest or ceased questing within 60 s an/or retreated from the treated area was recorded as repelled. Additionally, a qualified tick that crawled onto the treated area but fell off within an additional 60 s was recorded as repelled.

Each volunteer had 5 qualified ticks offered to each treated circle at approximately hourly intervals. Exposures continued until 3 out of any group of 5 offered ticks were deemed 'attracted'. The first non-repelled tick was defined as the first attracted tick which was followed by a second attracted tick within the same or following exposure period. The time of the first confirmed attracted tick was deemed to be the time at which complete repellency 'broke down' for that volunteer.

TABLE 16

Mean complete protection times for DHN, mDHN and DEET at 30% (w/v), topically applied to human volunteers, towards the deer tick *Ixodes scapularis*

| Repellent Treatment | Mean (SEM) |
| --- | --- |
| 30% DEET (positive control) | 124.0 (69.95) |
| 30% DHN | 109.0 (58.64) |
| 30% mDHN | 85.25 (28.76) |

The data (Table 16) indicates that DEET offered a mean complete protection time from the deer tick *Ixodes scapularis* of 124 min, whilst DHN was similarly effective for 109 min, and mDHN (mixed diastereomers of DHN) for 85 min. Thus it is clear that both DHN and mDHN are repellent towards the deer tick. An ANOVA of the protection times was conducted, which showed that DHN, mDHN and DEET were statistically indistinguishable in the longevity of their repellency to these ticks.

Example 9

Repellency of Dihydronepetalactones applied to Human Subjects Towards the Mosquito *Anopheles albimanus*

The DHN derived from hydrogenation of trans,cis-nepetalactone (consisting principally of 1S,9S,5R,6R-5,9-dimethyl-3-oxabicyclo[4.3.0]nonan-2-one; Formula 4), prepared as in Example 7, and the mixture of dihydronepetalactones prepared according to Example 2, were tested for repellency against *A. albimanus*, with DEET included in the test as a positive control, using adult human volunteers. Test cages (2×2×2 feet) with two sleeved entry ports on each of two opposite sides were used, with a hand rest in the center. The sides and top were screened and the base was equipped with a mirror to facilitate observations. Two hundred adult female mosquitoes, which had never received a blood meal and which had been deprived of their normal diet of 10% sucrose 24 h prior to use, were released into the test cage. Each volunteer was pre-qualified as attractive through having 10 insects land on their untreated forearms within 30 s of insertion into the cage.

A volume of 1.0 ml of each compound (either 5% or 10% (w/v) in isopropanol) was applied to 250 cm² areas on the forearms of six male human volunteers, the remainder of the limbs having been made inaccessible to insects. Each volunteer had different repellents applied individually onto each forearm. After allowing the applied repellents to dry for 30 min, the forearms were placed into the test cage for 5 min periods at 30 min intervals, and the number of mosquitoes probing or biting during each exposure period recorded. Breakdown of repellency was recorded for each repellent on each volunteer. Breakdown was defined as the time at which the first confirmed bite occurred; the first confirmed bite was defined as a bite which was followed by a second bite either within the same or the next exposure period. The data is presented in Table 17 as mean complete protection time. The data indicates that both DHN and mDHN conferred complete protection from bites for significant periods of time (eg., at 10% (w/v) for 3.5 and 5 hours, respectively), and comparable to that afforded by DEET at the same concentration.

The data was analyzed using ANOVA, and this showed that the 5% and 10% mDHN solutions were statistically indistinguishable in efficacy from 5% and 10% DEET, respectively. The 5% and 10% solutions of DHN, although statistically equal to the corresponding solutions of mDHN, provided lesser protection times.

TABLE 17

Mean complete protection times of dihydronepetalactones at 5% and 10% (w/v), topically applied to human volunteers, towards female *Anopheles albimanus* mosquitoes

| Repellent Treatment | Mean (h) (SEM) |
| --- | --- |
| 5% DEET (positive control) | 4.0 (0.5) |
| 5% DHN | 1.8 (0.12) |
| 5% mDHN | 3.0 (0.54) |
| 10% DEET (positive control) | 6.2 (0.63) |
| 10% DHN | 3.5 (0.29) |
| 10% mDHN | 5.0 (0.61) |

What is claimed is:

1. A method of preparing a composition comprising a dihydronepetalactone, or a mixture of dihydronepetalactone diastereomers, wherein a dihydronepetalactone is described generally by the following structure,

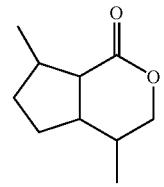

and wherein the method comprises:
 (a) providing an herbaceous material that comprises the genus *Nepeta* (catmint),
 (b) extracting from the herbaceous materials an oil that comprises nepetalactone,
 (c) contacting the oil with hydrogen in the presence of a hydrogenation catalyst, but in the absence of a diluent, to provide a dihydronepetalactone, and
 (d) recovering the dihydronepetalactone so produced and admixing it with a carrier and/or a cosmetic adjuvant.

2. A method according to claim 1 wherein the herbaceous material comprises the species *Nepeta Cateria*.

3. A method according to claim 2 wherein step (a) comprises selecting a chemotype of *Nepeta Cateria* that yields an oil comprising a greater amount of trans,cis-nepetalactone and/or cis,trans-nepetalactone than cis,cis-nepetalactone.

4. A method according to claim 2 wherein step (a) comprises selecting a chemotype of *Nepeta Cateria* that yields an oil comprising a greater amount of trans,cis-nepetalactone and/or cis,trans-nepetalactone than trans, trans-nepetalactone.

5. A method according to claim 1 wherein the hydrogenation catalyst comprises a material selected from the group consisting of iridium, palladium, rhodium, nickel, ruthenium, platinum, rhenium, combinations thereof, and compounds thereof; or the hydrogenation catalyst is supported on a support material selected from the group consisting of oxides, silica, alumina, titania, calcium carbonate, barium sulfate, and carbons.

6. A method according to claim 1 wherein oil is extracted from the herbaceous material by steam distillation.

7. A method of preparing a composition comprising a dihydronepetalactone, or a mixture of dihydronepetalactone diastereomers, wherein a dihydronepetalactone is described generally by the following structure,

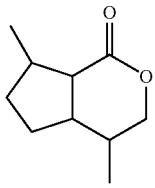

and wherein the method comprises:
(a) providing an herbaceous material that comprises the genus *Nepeta* (catmint),
(b) extracting from the herbaceous materials an oil that comprises nepetalactone,
(c) contacting the oil with hydrogen in the presence of a hydrogenation catalyst, and in the presence of an alcohol diluent, to provide a dihydronepetalactone, and
(d) recovering the dihydronepetalactone so produced as a mixture with the alcohol diluent.

8. A method according to claim 7 wherein step (d) further comprises distilling the mixture of dihydronepetalactone and alcohol diluent.

9. A method according to claim 7 wherein the herbaceous material comprises the species *Nepeta Cateria*.

10. A method according to claim 9 wherein step (a) comprises selecting a chemotype of *Nepeta Cateria* that yields an oil comprising a greater amount of trans,cis-nepetalactone and/or cis,trans-nepetalactone than cis,cis-nepetalactone.

11. A method according to claim 9 wherein step (a) comprises selecting a chemotype of *Nepeta Cateria* that yields an oil comprising a greater amount of trans,cis-nepetalactone and/or cis,trans-nepetalactone than trans, trans-nepetalactone.

12. A method according to claim 7 wherein the hydrogenation catalyst comprises a material selected from the group consisting of iridium, palladium, rhodium, nickel, ruthenium, platinum, rhenium, combinations thereof, and compounds thereof; or the hydrogenation catalyst is supported on a support material selected from the group consisting of oxides, silica, alumina, titania, calcium carbonate, barium sulfate, and carbons.

13. A method according to claim 7 wherein oil is extracted from the herbaceous material by steam distillation.

14. A method according to claim 1 wherein the nepetalactone is a 7-S nepetalactone, and the dihydronepetalactone is a 9-S dihydronepetalactone, or mixture of diastereomers thereof.

15. A method according to claim 7 wherein the nepetalactone is a 7-S nepetalactone, and the dihydronepetalactone is a 9-S dihydronepetalactone, or mixture of diastereomers thereof.

* * * * *

UNITED STATES PATENT AND TRADEMARK OFFICE
CERTIFICATE OF CORRECTION

PATENT NO. : 7,547,793 B2
APPLICATION NO. : 11/474595
DATED : June 16, 2009
INVENTOR(S) : David L. Hallahan et al.

Page 1 of 1

It is certified that error appears in the above-identified patent and that said Letters Patent is hereby corrected as shown below:

On the title page, below "(*) Notice: Subject to any disclaimer, the term of this patent is extended or adjusted under 35 U.S.C. 154(b) by 203 days."

insert

--This patent is subject to a terminal disclaimer--.

Signed and Sealed this

Twenty-eighth Day of July, 2009

JOHN DOLL
*Acting Director of the United States Patent and Trademark Office*